United States Patent
Brody et al.

(10) Patent No.: US 12,150,655 B2
(45) Date of Patent: Nov. 26, 2024

(54) AUTOMATED CRANIAL BURR HOLE DEVICE AND METHOD

(71) Applicants: The Henry M. Jackson Foundation for the Advancement of Military Medicine, Inc., Bethesda, MD (US); The Johns Hopkins University, Baltimore, MD (US)

(72) Inventors: David L. Brody, Bethesda, MD (US); David Blodgett, Ellicott City, MD (US); Adam Cohen, Baltimore, MD (US); Max R. Basescu, Baltimore, MD (US); Kevin C. Wolfe, Lutherville, MD (US); Jared M. Wormley, Silver Spring, MD (US)

(73) Assignees: The Henry M. Jackson Foundation for the Advancement of Military Medicine, Inc., Bethesda, MD (US); The Johns Hopkins University, Baltimore, MD (US)

( * ) Notice: Subject to any disclaimer, the term of this patent is extended or adjusted under 35 U.S.C. 154(b) by 268 days.

(21) Appl. No.: 17/627,567

(22) PCT Filed: Jul. 16, 2020

(86) PCT No.: PCT/US2020/042370
§ 371 (c)(1),
(2) Date: Jan. 14, 2022

(87) PCT Pub. No.: WO2021/011795
PCT Pub. Date: Jan. 21, 2021

(65) Prior Publication Data
US 2022/0257266 A1 Aug. 18, 2022

Related U.S. Application Data

(60) Provisional application No. 62/874,823, filed on Jul. 16, 2019.

(51) Int. Cl.
*A61B 17/16* (2006.01)
*A61B 5/03* (2006.01)
(Continued)

(52) U.S. Cl.
CPC ......... *A61B 17/1695* (2013.01); *A61B 5/031* (2013.01); *A61B 17/1739* (2013.01);
(Continued)

(58) Field of Classification Search
CPC .................................................. A61B 17/1695
See application file for complete search history.

(56) References Cited

U.S. PATENT DOCUMENTS

| 3,457,922 A | 7/1969 | Ray |
| 4,699,550 A | 10/1987 | Baker |

(Continued)

FOREIGN PATENT DOCUMENTS

CN          108567467 A       9/2018

OTHER PUBLICATIONS

Ferrari, M., and Quaresima, V. (Mar. 2012). "A brief review on the history of human functional near-infrared spectroscopy (fNIRS) development and fields of application," Neuroimage, 63, pp. 1-15.
(Continued)

*Primary Examiner* — Olivia C Chang
(74) *Attorney, Agent, or Firm* — Foley & Lardner LLP

(57) ABSTRACT

An intracranial access device includes a housing having an operator-facing side and a patient-facing side and an opening therethrough extending from the operator-facing side to the patient-facing side. The device further includes at least one fastener configured to secure the device to a cranium of a patient. The device further includes a drill mounted to a surface of the housing and a cauterizer. The device may further include a number of sensors arranged on the patient-
(Continued)

facing side of the housing and configured to identify a hemorrhage location.

13 Claims, 34 Drawing Sheets

(51) Int. Cl.
    *A61B 17/17*     (2006.01)
    *A61B 18/14*     (2006.01)
    *A61B 90/11*     (2016.01)
    *A61N 1/05*     (2006.01)
    *A61B 18/00*     (2006.01)
    *A61B 90/00*     (2016.01)
    *A61B 90/10*     (2016.01)

(52) U.S. Cl.
    CPC .......... *A61B 18/1402* (2013.01); *A61B 90/11* (2016.02); *A61N 1/0539* (2013.01); *A61B 2018/00321* (2013.01); *A61B 2018/00565* (2013.01); *A61B 2018/00595* (2013.01); *A61B 2018/00791* (2013.01); *A61B 2090/033* (2016.02); *A61B 2090/064* (2016.02); *A61B 2090/103* (2016.02); *A61B 2090/374* (2016.02); *A61B 2090/3762* (2016.02); *A61B 2217/005* (2013.01); *A61B 2218/007* (2013.01)

(56) References Cited

U.S. PATENT DOCUMENTS

| | | | |
|---|---|---|---|
| 5,360,427 | A | 11/1994 | Majlessi |
| 6,129,731 | A | 10/2000 | Haeusler et al. |
| 9,101,756 | B1 | 8/2015 | Pianca et al. |
| 2001/0016744 | A1* | 8/2001 | Kupferschmid ... A61B 17/1695 606/80 |
| 2003/0149442 | A1 | 8/2003 | Gellman et al. |
| 2004/0243145 | A1* | 12/2004 | Bobo, Sr. ........... A61B 17/1695 606/129 |
| 2009/0203983 | A1 | 8/2009 | Carlton et al. |
| 2011/0040304 | A1 | 2/2011 | Li et al. |
| 2011/0054518 | A1 | 3/2011 | Carbunaru et al. |
| 2013/0019877 | A1 | 1/2013 | Sklar |
| 2013/0085400 | A1 | 4/2013 | Oliveira et al. |
| 2016/0157766 | A1 | 6/2016 | Simpson et al. |
| 2017/0119527 | A1 | 5/2017 | Chavez et al. |
| 2021/0085342 | A1* | 3/2021 | Ayer ................. A61B 17/1739 |

OTHER PUBLICATIONS

Hawrysz, D.J., and Sevick-Muraca, E.M., "Developments toward diagnostic breast cancer imaging using near-infrared optical measurements and fluorescent contrast agents", Neoplasia (Sep.-Oct. 2000), vol. 2, No. 5, pp. 388-417.

Liu, J. T. et al., "Emergency management of epidural haematoma through burr hole evacuation and drainage. A preliminary report", Acta Neurochirurgica (Wien) (Jan. 2006), 148: pp. 313-317.

Krauss, S. et al., "Quickly Evaluating an Emerging Medical Technology Using Feedback From the Field: A Case Study of the BrainScope One and Infrascanner 2000 User Evaluation," Military Medicine, 2020, pp. 1-7, retrieved Jun. 23, 2020.

Shrestha, D. and Feng, L., "A Novel Surgical Approach to Traumatic Intracranial Epidural Hematoma", Open Access Library Journal (Aug. 8, 2017), 4:e3820 (11 pages).

Tromberg, B.J. et al., "Non-invasive in vivo characterization of breast tumors using photon migration spectroscopy", Neoplasia (Jan.-Apr. 2000), vol. 2, Nos. 1-2, pp. 26-40.

Wilson, M.H., et al., "Emergency burr holes: How to do it", Scandinavian Journal of Trauma, Resuscitation, and Emergency Medicine (Apr. 2, 2012), 20:24.

\* cited by examiner

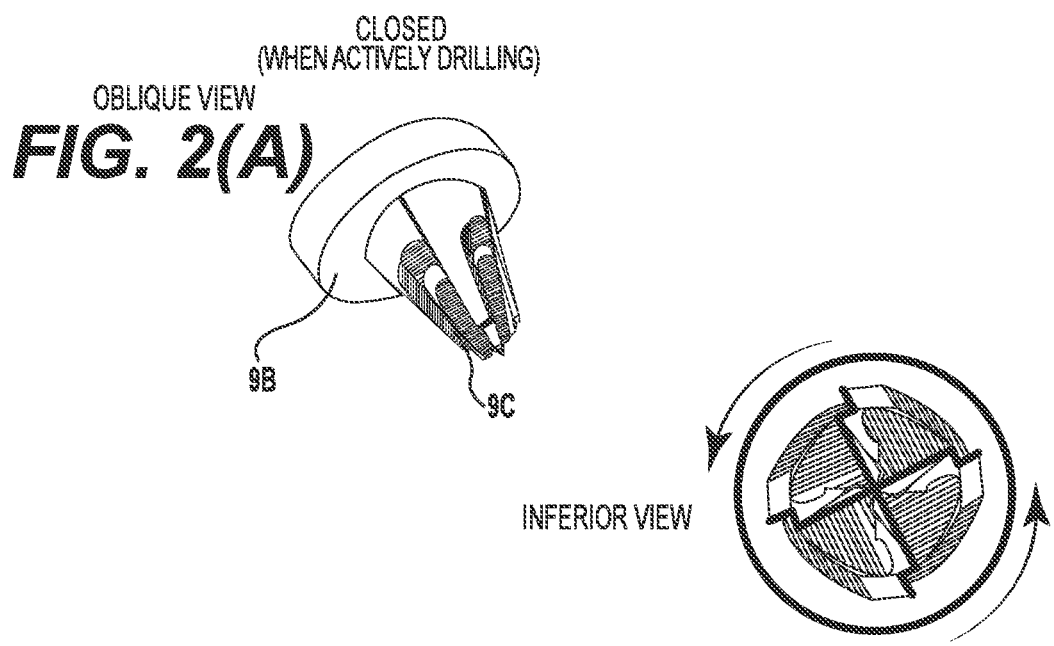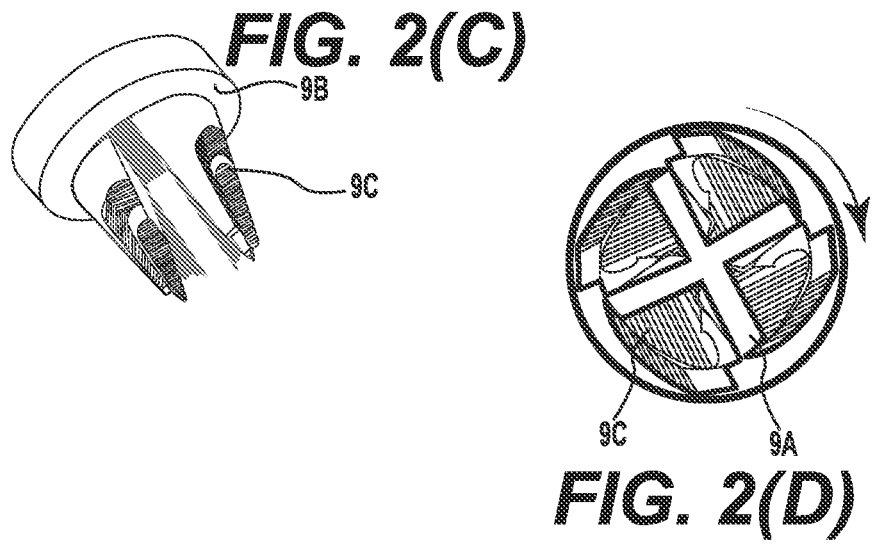

RETRACTOR BLADE IS CURVED.
PANELS OF BLADE ARE SPRING LOADED
AND OPEN UPON RELEASE UPON DEPLOYMENT.
PROTECTS SKIN FROM DRILL.

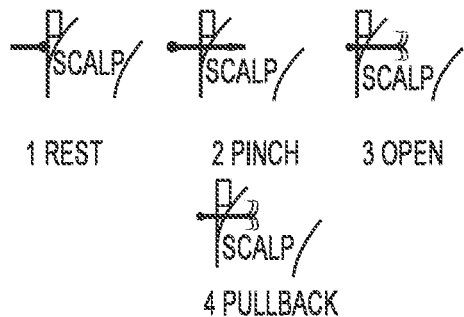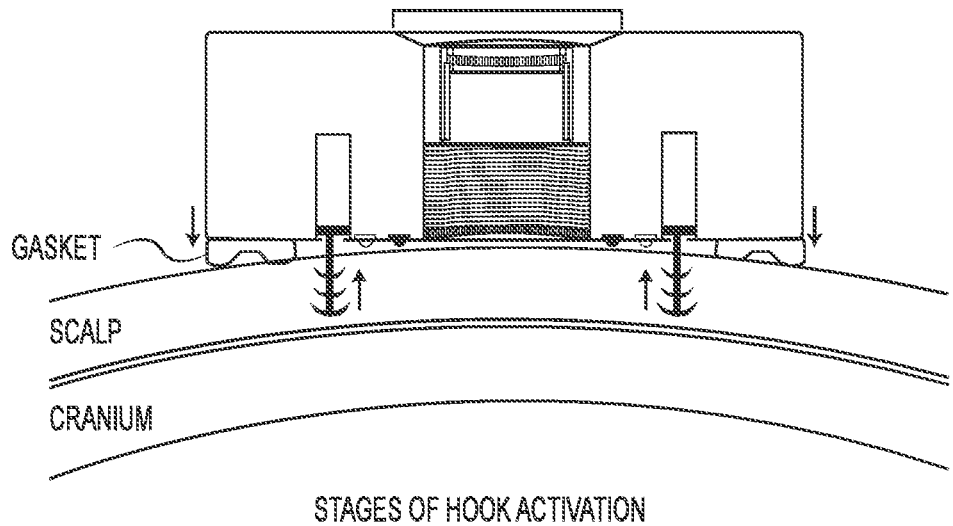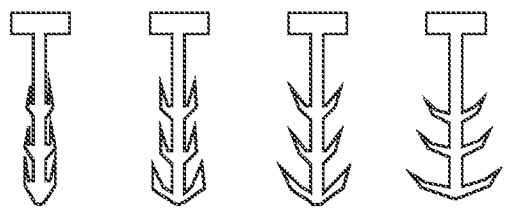
FIG. 7

DURING DRILLING THROUGH CRANIUM

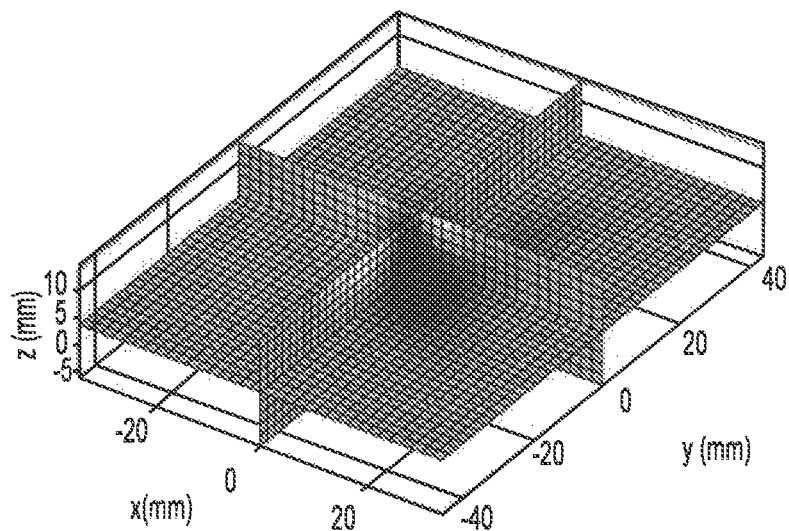
FIG. 23(A)
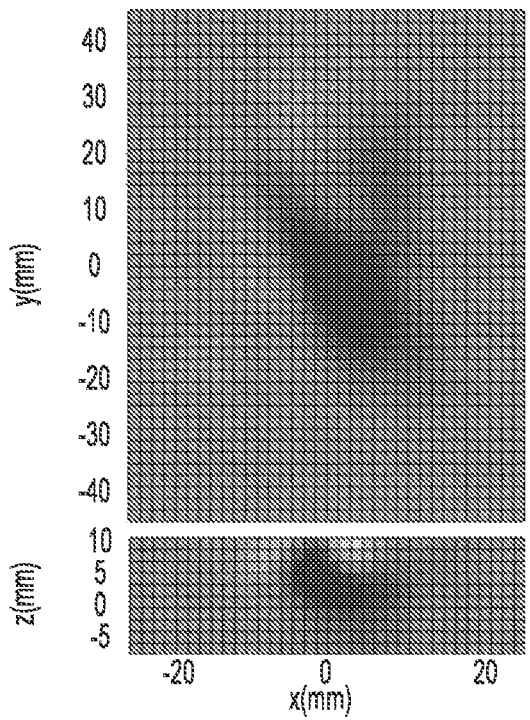
FIG. 23(B)
FIG. 23(C)

AUTOMATED CRANIAL BURR HOLE DEVICE AND METHOD

CROSS-REFERENCE TO RELATED APPLICATIONS

This application claims the benefit of priority to U.S. Provisional Patent Application No. 62/874,823, filed on Jul. 16, 2019, the entire contents of which are incorporated by reference herein.

STATEMENT REGARDING FEDERALLY SPONSORED RESEARCH OR DEVELOPMENT

This invention was made with government support under HU0001-17-2-0029 awarded by the Uniformed Services University of the Health Sciences. The government has certain rights in the invention.

FIELD

The present disclosure describes devices and methods for creating burr holes in a cranium. The devices and methods can be used to relieve intracranial pressure, such as may arise from subdural or epidural hemorrhage, and to monitor intracranial pressure, such as in the event of diffuse swelling. The present disclosure also describes devices and methods for visualizing and localizing intracranial pathology, such as hemorrhage.

BACKGROUND

To treat a patient suffering from a condition such as a traumatic epidural hemorrhage (EDH) or a subdural hemorrhage (SDH) and/or to monitor intracranial pressure, it may be necessary to drill one or more burr holes in the patient's skull. The burr holes may help to relieve pressure on the brain when fluid (e.g., blood) builds up just below the dura mater, so as to prevent the fluid from compressing brain tissue and/or to provide intracranial access. The window of opportunity for diagnosing and treating EDH or SDH is short. Thus, there is a need for devices and methods for creating burr holes in a cranium.

There also is a need for devices and methods for visualizing and localizing intracranial pathology, such as hemorrhage, that can be used in the field to identify, localize and/or facilitate treatment of EDH and/or SDH.

SUMMARY

In accordance with some embodiments, there are provided devices for creating burr holes in a cranium and methods for creating burr holes in a cranium.

In accordance with some embodiments, an intracranial access device includes a housing having an operator-facing side and a patient-facing side and an opening therethrough extending from the operator-facing side to the patient-facing side. The device may further include a plurality of fasteners deployably housed in the patient-facing side of the housing configured to secure the device to the cranium. The device may further include a plurality of sensors arranged on the patient-facing side of the housing and configured to identify a hemorrhage location. The device may further include a sealing member configured to form a seal between the housing and the surface of a patient's head. The device may further include a membrane covering the opening on the operator-facing side of the housing. The device may further include a retractor housed within the housing including retractor blades structured to cut into the scalp. The device may further include a drill housed within the housing, structured to penetrate into the cranium.

In accordance with some embodiments, a method for relieving intracranial pressure of a patient in need thereof incudes positioning an intracranial access device as described herein on a surface of the patient's head, activating the intracranial access device to create an intracranial burr hole, and withdrawing intracranial fluid through the intracranial burr hole, thereby relieving intracranial pressure.

In accordance with some embodiments, a method for monitoring intracranial pressure of a patient in need thereof incudes positioning an intracranial access device as described herein on a surface of the patient's head, activating the intracranial access device to create an intracranial burr hole, and inserting an intracranial pressure monitor through the intracranial burr hole.

In accordance with some embodiments, a system for providing intracranial access while reducing the risk of intracranial infection includes a housing having an operator-facing side and a patient-facing side and an opening therethrough extending from the operator-facing side to the patient-facing side, a gasket configured to form a seal between the housing and the surface of a patient's head and a membrane covering the opening on the operator side. The system may further include a plurality of fasteners deployably housed in the patient-facing side of the housing configured to secure the device to the cranium. The system may further include a retractor including retractor blades structured to be operated through the opening of the housing and cut into and retract the scalp. The system may further include a drill structured to be operated through the opening of the housing and penetrate into a cranium, and powered by a power source. The system may further include the power source. The system may further include an intracranial monitor structured to be inserted through the opening of the housing, and powered by a power source.

According to a first specific embodiment of the present disclosure, an intracranial access device includes a housing having an operator-facing side and a patient-facing side and an opening therethrough extending from the operator-facing side to the patient-facing side, configured to accommodate access to a treatment area, wherein the housing includes a surface positioned on the operator-facing side, at least one fastener configured to secure the device to a cranium of the patient, a drill mounted to the surface and structured to penetrate into the cranium, and a cauterizer mounted to the surface and configured to cauterize the treatment area.

In any embodiments, the at least one fastener may include adhesive, which optionally may comprise an open-cell foam, such as cyanoacrylate. In any embodiments, the at least one fastener may include a number of bone screws. In any embodiments, the device may further include a sealing member disposed on the patient-facing side of the housing and configured to seal the device to a patient, which optionally may comprise a closed-cell foam. In any embodiments, the device may further include a storage cap configured to protect the sealing member from contaminants until use.

In any embodiments, the cauterizer may include an electrocautery element, and may optionally further include a power source configured to power the electrocautery element. In any embodiments, the cauterizer may include a plunger, wherein operation of the cauterizer includes depressing the plunger such that electrocautery element contacts the treatment surface. In any embodiments, the cauterizer may be axially aligned with the opening.

In any embodiments, the device may further include a membrane configured to seal the opening, the membrane being penetrable to provide access to the treatment area.

In any embodiments, at least a portion of the housing may be selectively rotatable to facilitate alternating between drilling and access to the treatment area. In any such embodiments, the housing may include a user interface to facilitate locking a rotational position of the surface.

According to a second specific embodiment of the present disclosure, an electronic device for identifying an intracranial hemorrhage location in a patient includes one or more light transmitters configured to transmit intensity modulated light into tissue of the patient, one or more sensors configured to measure an amplitude and phase shift of light reflected from the tissue, and a processing circuit including a processor and memory, the memory having instructions stored thereon that, when executed by the processor, cause the processing circuit to receive the measured amplitude and the phase shift of the reflected light and detect an intracranial hemorrhage based on the intensity and the phase shift of the reflected light. In any embodiments, the device may further include one or more light guides configured to direct the frequency modulated light from the one or more light transmission elements into the tissue.

In any embodiments, detecting the intracranial hemorrhage includes quantitative measurement of optical properties of the tissue including the intensity of the reflected light. In any embodiments, a determination may be made as to whether the quantitative measurement in a specific location matches to values expected for hemorrhage. Optionally, the determination may be made with reference to a threshold. In any embodiments, detecting the intracranial hemorrhage may include generating a baseline absorption associated with the tissue based on the intensity of the reflected light and identifying an area of the tissue having an absorption a threshold amount below the baseline absorption. In any embodiments, detecting the intracranial hemorrhage may include generating a baseline phase shift associated with the tissue based on the phase shift of the reflected light and identifying an area of the tissue having a phase shift a threshold amount away from the baseline phase shift. In any embodiments, the instructions may further cause the processing circuit to generate a three-dimensional map of the tissue illustrating absorption values. In any embodiments, the instructions may further cause the processing circuit to generate an estimate of a size of the detected intracranial hemorrhage.

According to a third specific embodiment, a method for relieving intracranial pressure in a patient in need thereof includes operating a frequency-domain diffuse optical tomography (FD-DOT) handheld device to identify a location of the intracranial pressure, positioning an intracranial access device on a surface of the patient's head at the identified location, operating the intracranial access device to create an intracranial burr hole, and withdrawing intracranial fluid through the intracranial burr hole, thereby relieving the intracranial pressure. In any embodiments, the frequency-domain diffuse optical tomography (FD-DOT) handheld device may be a device as described herein. In any embodiments, the intracranial access device may be an intracranial access device as described herein.

BRIEF DESCRIPTION OF THE DRAWINGS

The details of one or more embodiments are set forth in the accompanying drawings and the description below. In the drawings, like reference numerals are used throughout the various views to designate like components. The drawings are merely exemplary to illustrate certain features that may be used singularly or in combination with other features and the present application should not be limited to the embodiments shown.

FIG. 2(A) is a front perspective view of a drill bit in an active state, according to at least one embodiment described herein.

FIG. 2(B) is a rear view of a drill bit in an active state, according to at least one embodiment described herein.

FIG. 2(C) is a front perspective view of a drill bit in an inactive state, according to at least one embodiment described herein.

FIG. 2(D) is a rear view of a drill bit in an inactive state, according to at least one embodiment described herein.

FIG. 7 depicts a bottom view of an intracranial access device including fasteners, as shown in a deployed state, according to at least one embodiment described herein.

FIG. 23(A) illustrates a three-dimensional plot of absorption values determined by measuring tissue using FD-DOT, according to at least one exemplary embodiment.

FIG. 23(B) illustrates a two-dimensional plot of absorption values determined by measuring tissue using FD-DOT, according to at least one exemplary embodiment.

FIG. 23(C) illustrates a two-dimensional plot of absorption values determined by measuring tissue using FD-DOT, according to at least one exemplary embodiment.

DETAILED DESCRIPTION

Figure 1A:
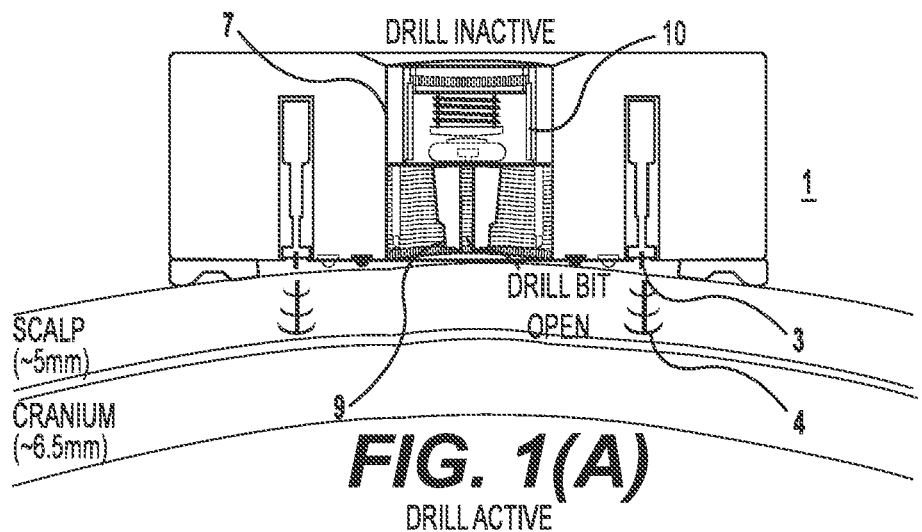
FIG. 1(A) is a lateral view of a portion of an intracranial access device in an inactive state, according to at least one embodiment described herein.
Figure 1B:
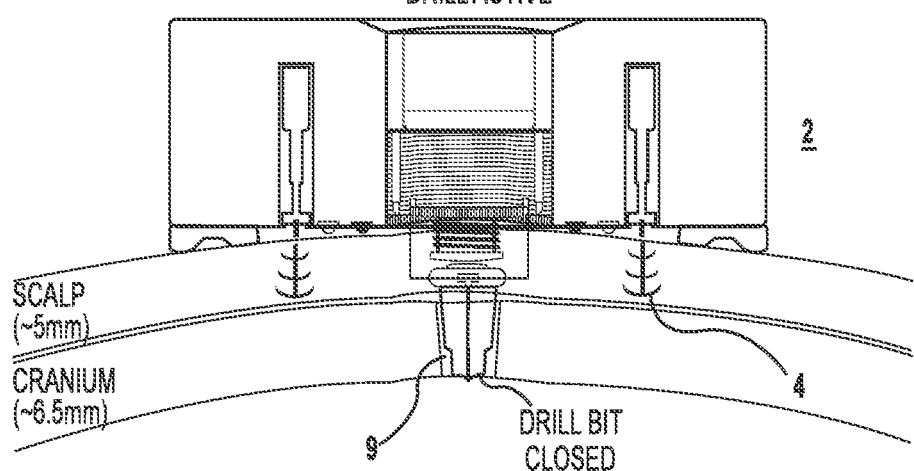
FIG. 1(B) is a lateral view of an intracranial access device in an active state, according to at least one embodiment described herein.

The following detailed description is presented to enable any person skilled in the art to make and use the subject of the application. For purposes of explanation, specific nomenclature is set forth to provide a thorough understanding of the present disclosure. However, it will be apparent to one skilled in the art that these specific details are not required to practice the subject of the application. Descriptions of specific applications are provided only as representative examples. The present application is not intended to be limited to the embodiments shown but is to be accorded the widest possible scope consistent with the principles and features disclosed herein.

Described herein are devices and methods for detection and treatment of subdural hematomas (SDH) and epidural hematomas (EDH). In various embodiments, the devices and methods of the present disclosure are usable to relieve intracranial pressure. Additionally or alternatively, the devices and methods may be used to monitor intracranial pressure, such as in the event of diffuse swelling. The compact size and ease of use of the devices make them particularly useful in field environments.

Brain surgery is often performed in resource-rich environments such as hospitals and clinical settings under relatively sterile conditions, and is often planned well in advance of when it takes place. However, in field settings, resources may be spare. Examples of field settings include, but are not limited to, remote operating bases and other locations where military medical personnel and others provide medical care without access to immediate neurosurgical care and facilities, such as combat medics, field medics, wilderness medics, field workers, shipboard medics, aeromedical personnel, medical evacuation specialists, rural health care providers, and paramedics in mass causalities or other emergency situations.

When diagnosis and treatment of conditions resulting in intracranial pressure are needed in such environments, benefits such as resources, pristine conditions, and time are generally lacking. For example, the equipment, care facilities, and personnel available to diagnose and treat conditions such as traumatic epidural hemorrhage (EDH) and subdural hemorrhage (SDH) may be absent or inaccessible. The window of opportunity to diagnose and treat such conditions may be short. For these reasons, the current state of field-based care of EDH and SDH leaves much to be desired.

The present disclosure relates to devices and methods useful for diagnosing and treating EDH and SDH in the field, and monitoring intracranial pressure, such as in the event of diffuse swelling. Exemplary devices disclosed herein are configured to detect and localize intracranial (e.g., epidural or subdural) hemorrhages and provide intracranial access for diagnostic and management tools and/or treatment. It is contemplated that the devices and methods could be used and practiced by persons other than neurosurgeons, by providing intracranial visualization and access in the field without neurosurgeons, hospital-based imaging equipment, or operating rooms. Use of the devices and methods may provide critically injured patients additional time to obtain additional care. While the devices and methods are described herein in the context of EDH and SDH, they can be used to diagnose and treat other conditions, such as other conditions where it is necessary or desirable to create burr holes in a cranium.

Certain embodiments are described hereinafter. It should be noted that the specific embodiments are not intended as an exhaustive description or as a limitation to the broader aspects discussed herein. Features described in conjunction with a particular embodiment are not necessarily limited to that embodiment, and may pertain to other embodiment(s).

Intracranial Access Device

In at least some embodiments described herein, an intracranial access device comprises (i) a housing having an operator-facing side and a patient-facing side and an opening therethrough extending from the operator-facing side to the patient-facing side, configured to accommodate an intracranial drill, (ii) a plurality of fasteners deployably housed in the patient-facing side of the housing configured to secure the device to the cranium (such as plurality of fasteners generally surrounding the opening and/or distributed around the circumference of the patient-facing side of the housing), and (iii) a plurality of sensors arranged on the patient-facing side of the housing and configured to identify a hemorrhage location. The device may further include a sealing member configured to form a seal between the housing and the surface of a patient's head. The device may further include a membrane covering the opening on the operator-facing side of the housing configured to provide a barrier between the interior of the housing and the external environment.

The device may further include a hollow drill housed within the opening of the housing, structured to penetrate into the cranium. In some embodiments, the hollow drill comprises a drill bit that has a closed position and an open position, wherein the drill bit is structured to penetrate the cranium in the closed position and allow passage of one or more objects or fluid through the drill bit in the open position.

The device may further include a retractor including retractor blades structured to cut into and retract the scalp. The retractor may be housed within the housing or associated with the drill.

In some embodiments, the device is provided with an external power supply, such as an external power supply configured to deliver power to the drill or other aspect of the device, such as solar power, battery power, or manual power (such as via a hand crank).

In some embodiments, an intracranial access device as described herein may be used as a system for providing intracranial access while reducing the risk of intracranial infection. Such a system may include, for example, a housing having an operator-facing side and a patient-facing side and an opening therethrough extending from the operator-facing side to the patient-facing side, a gasket configured to form a seal between the housing and the surface of a patient's head and a membrane covering the opening on the operator side. The system may further include a plurality of fasteners housed in the patient-facing side of the housing configured to secure the device to the cranium. The system may further include a retractor including retractor blades structured to cut into and retract the scalp. The system may further include a drill structured to be operated through the opening of the housing and penetrate into a cranium, and powered by a power source. The system may further include an intracranial monitor structured to be inserted through the opening of the housing, and powered by a power source. The system may further include a power source.

These components and others are discussed below.

Turning now to FIGS. 15(A)-(J), a device, shown as access device 1500, for providing intracranial access is shown, according to an exemplary embodiment. In various embodiments, access device 1500 facilitates perforation of the cranium to facilitate treatment and/or monitoring of intracranial pressure. Access device 1500 may be the same as and/or similar to intracranial access device 1 described below. For example, access device 1500 may share at least some of the elements and/or components of intracranial access device 1. Access device 1500 may be a handheld device that facilitates the creation of burr holes in austere environments and/or by individuals without extensive medical training and/or knowledge. For example, access device 1500 may be usable by a layperson in a non-medical environment such as a field location, forward-operating base or campsite. In various embodiments, access device 1500 includes housing 1510, drill 1540, cauterizer 1570, and access hole 1590. Components of access device 1500 are described in detail below.

Housing

Figure 4:
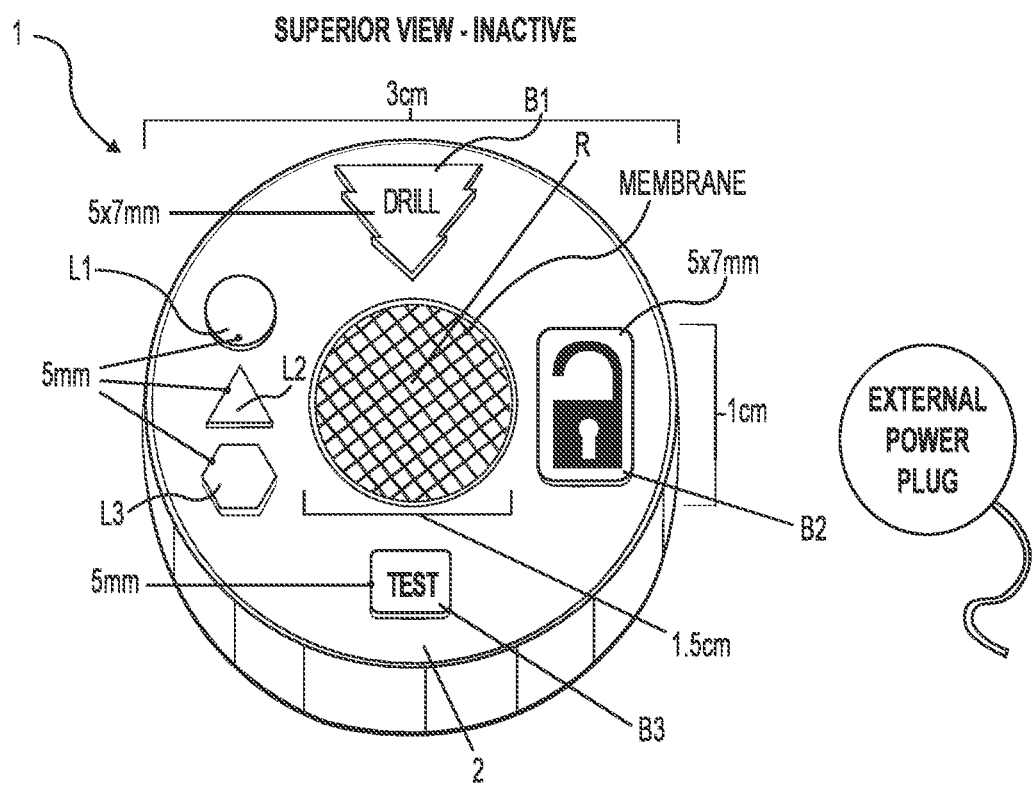
FIG. 4 depicts a top view of an intracranial access device according to at least one embodiment described herein.
Figure 6:
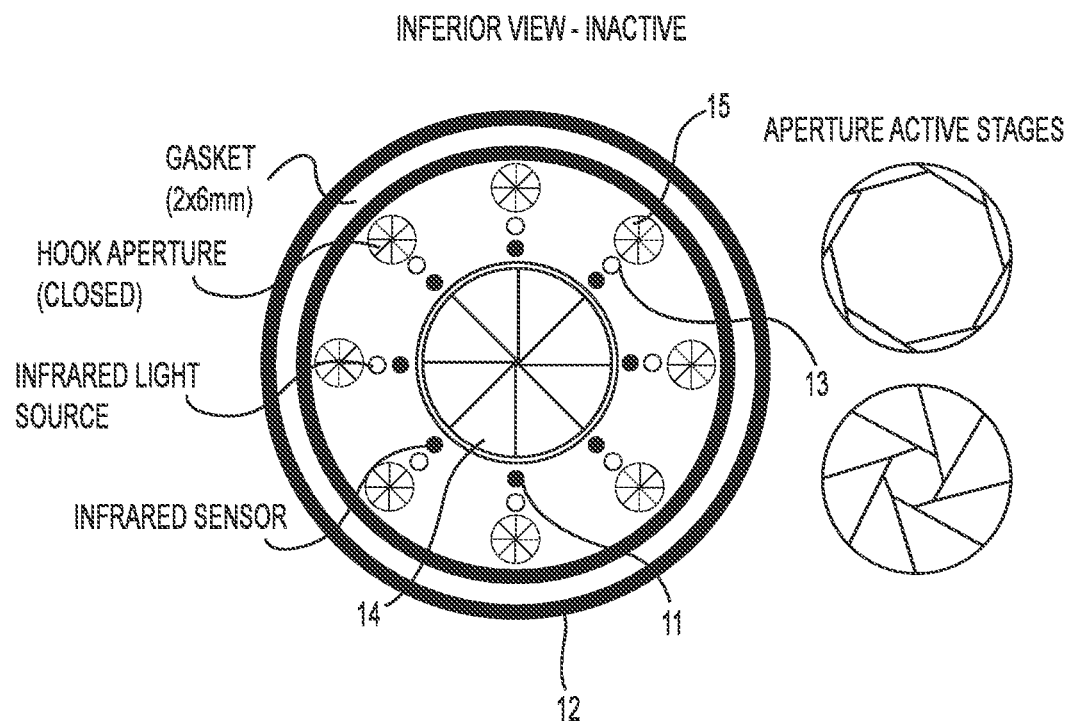
FIG. 6 depicts a bottom view of an intracranial access device in an inactive state, according to at least one embodiment described herein.

FIG. 4 depicts a top view of an intracranial access device 1 according to at least one embodiment. The intracranial access device includes a housing 2 that is configured to cover a region of interest on a patient's cranium, e.g., a region identified as having or suspected of having a hemorrhage. More specifically, the housing 2 is constructed to lie atop part of a patient's head, preferably a shaved or bald head. In some embodiments, the housing 2 comprises a gasket 12 that acts as a seal to seal the device to the head, as depicted in FIG. 6 and discussed further below. The housing 2 may be, for example, approximately 3 cm in diameter and approximately 1 cm thick, although the housing 2 is not limited to a circular footprint and/or the noted dimensions.

The housing 2 may be configured to include, on an operator-facing surface thereof, one or more indicators (e.g., light-emitting diodes (LEDs) optionally configured to emit light of a particular color in response to a signal). For example, FIG. 4 illustrates LEDs L1, L2 and L3 positioned on an operator-facing side of housing 2. As an illustrative example, L1 may be a green LED indicating a first detection result; L2 may be an orange or yellow LED indicating a second detection result, and L3 may be a red LED indicating a third detection result.

The housing 2 may further be outfitted with a plurality of buttons (e.g., B1, B2 and B3) for operating or deploying various functionalities of the device. As an illustrative example, button B1 may be a drill button which may be actuated (e.g., by pressing, flicking, switching or otherwise contacting) to cause a drill (discussed in more detail below) to be switched from an ON state to an OFF state or vice versa. Button B2 may be a "lock" button which, when actuated, causes the intracranial access device 1 deploy fasteners to lock the device in place on the patient's cranium. Button B3 may be a test button which, when actuated, causes control circuitry of the device 1 to execute a self-diagnostic test.

The housing 2 has an opening, typically at a center thereof. A membrane R (discussed below in more detail) is positioned so as to cover the opening on the operator-facing side of the housing. In some embodiments, a retractor 5 and/or drill 7 is housed within the opening of the housing.

Figure 15A:
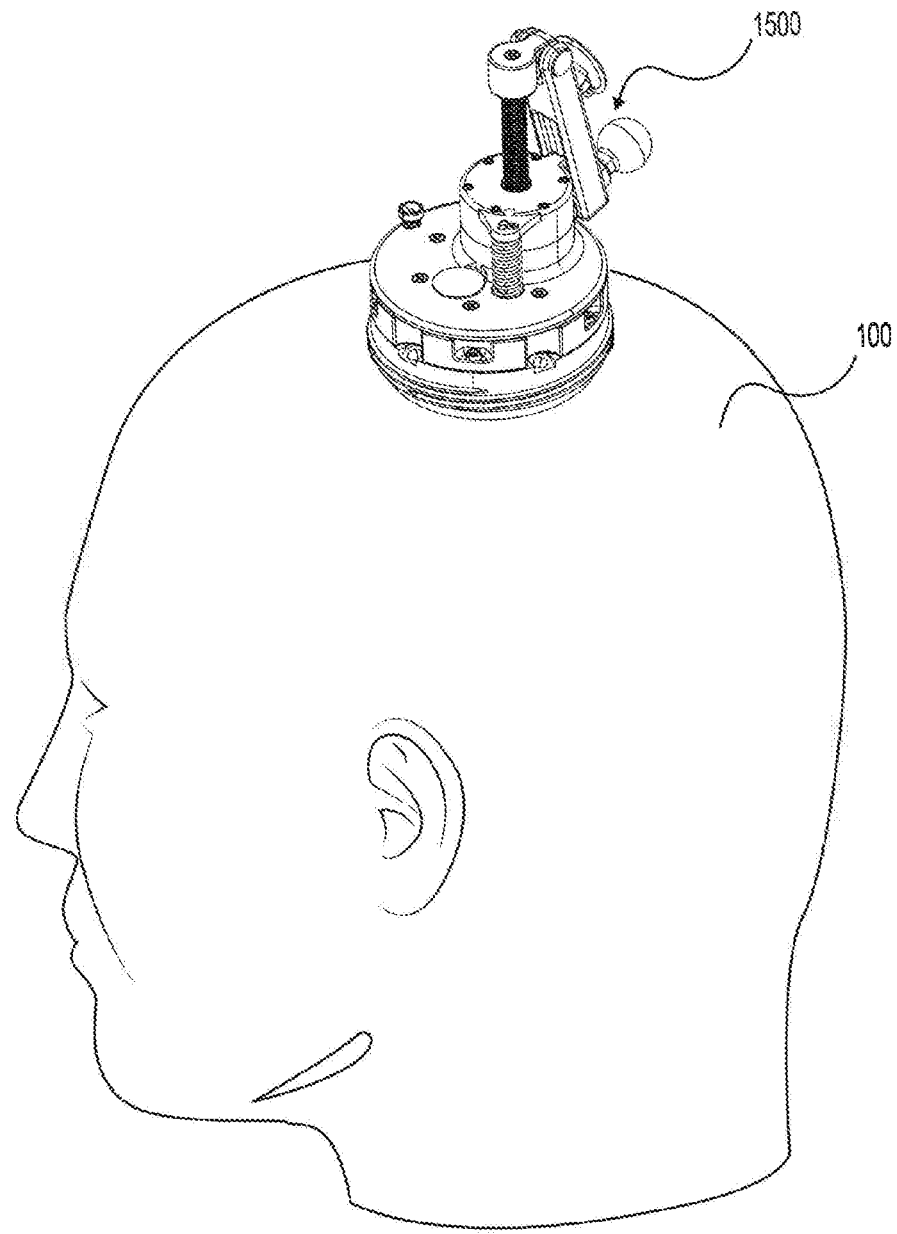
FIG. 15(A) illustrates a perspective view of a device as described herein for providing intracranial access, according to at least one exemplary embodiment.
Figure 15B:
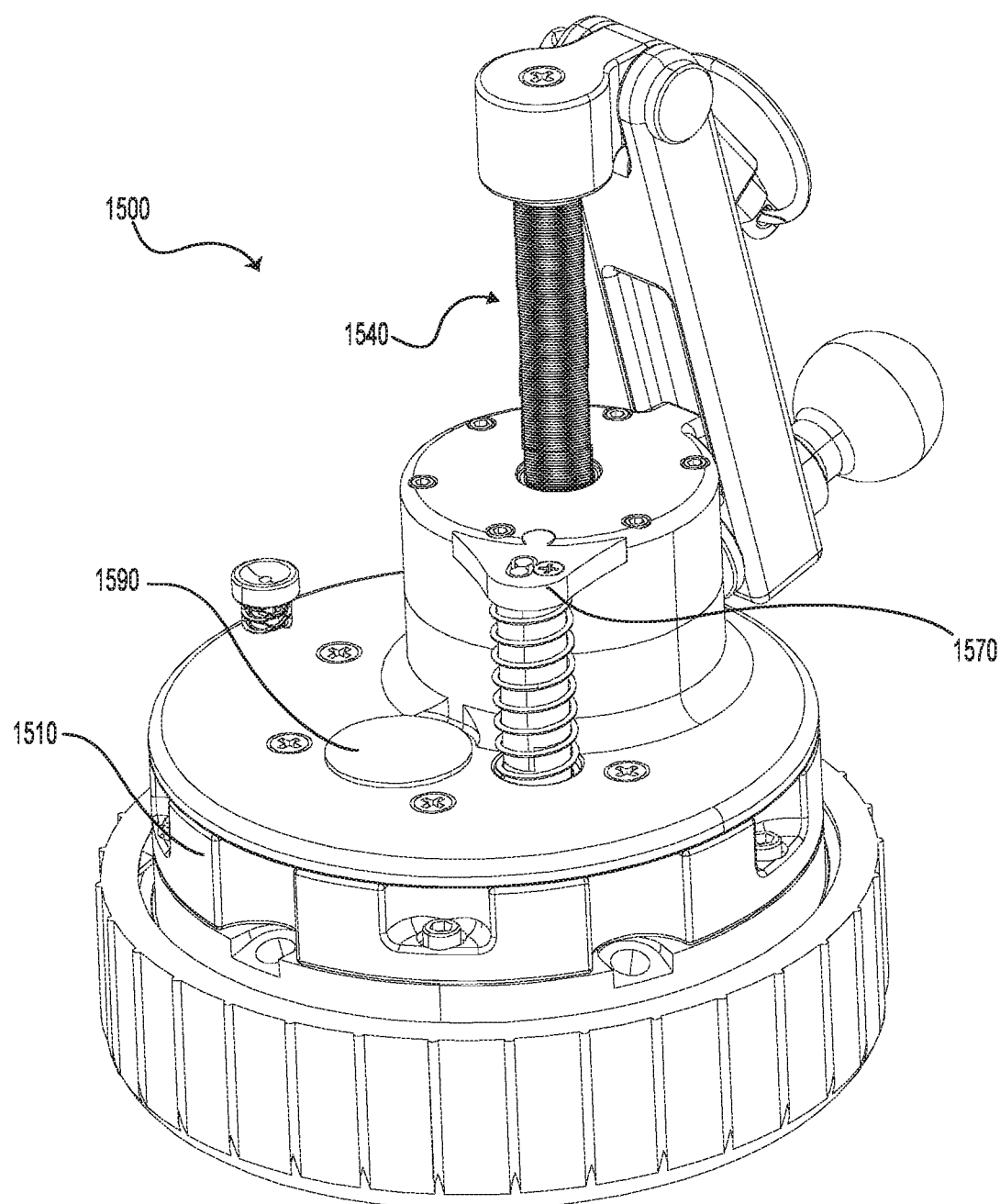
FIG. 15(B) is an enlarged view of the device shown in FIG. 15(A).
Figure 15C:
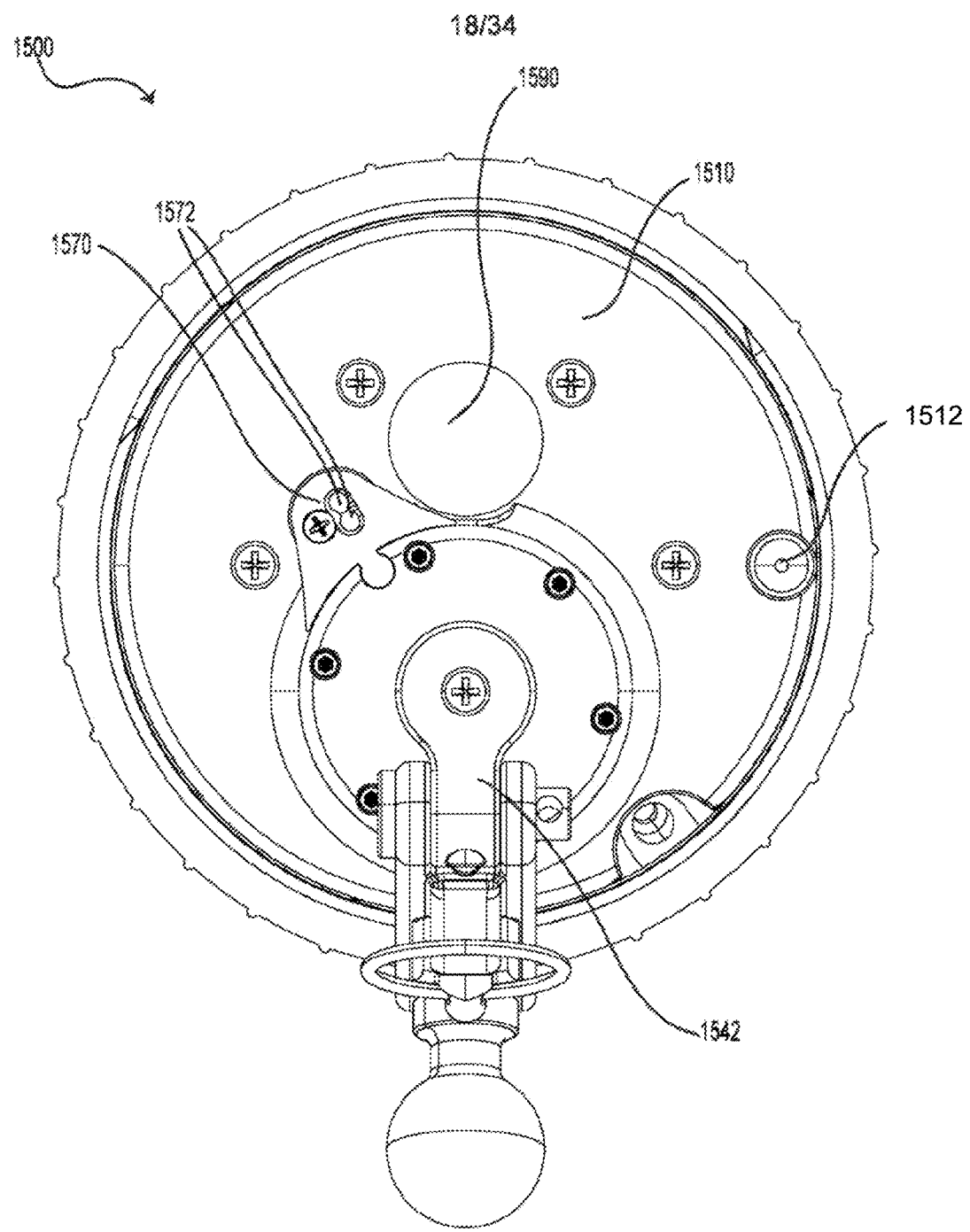
FIG. 15(C) is a top view of the device shown in FIG. 15(A).
Figure 15D:
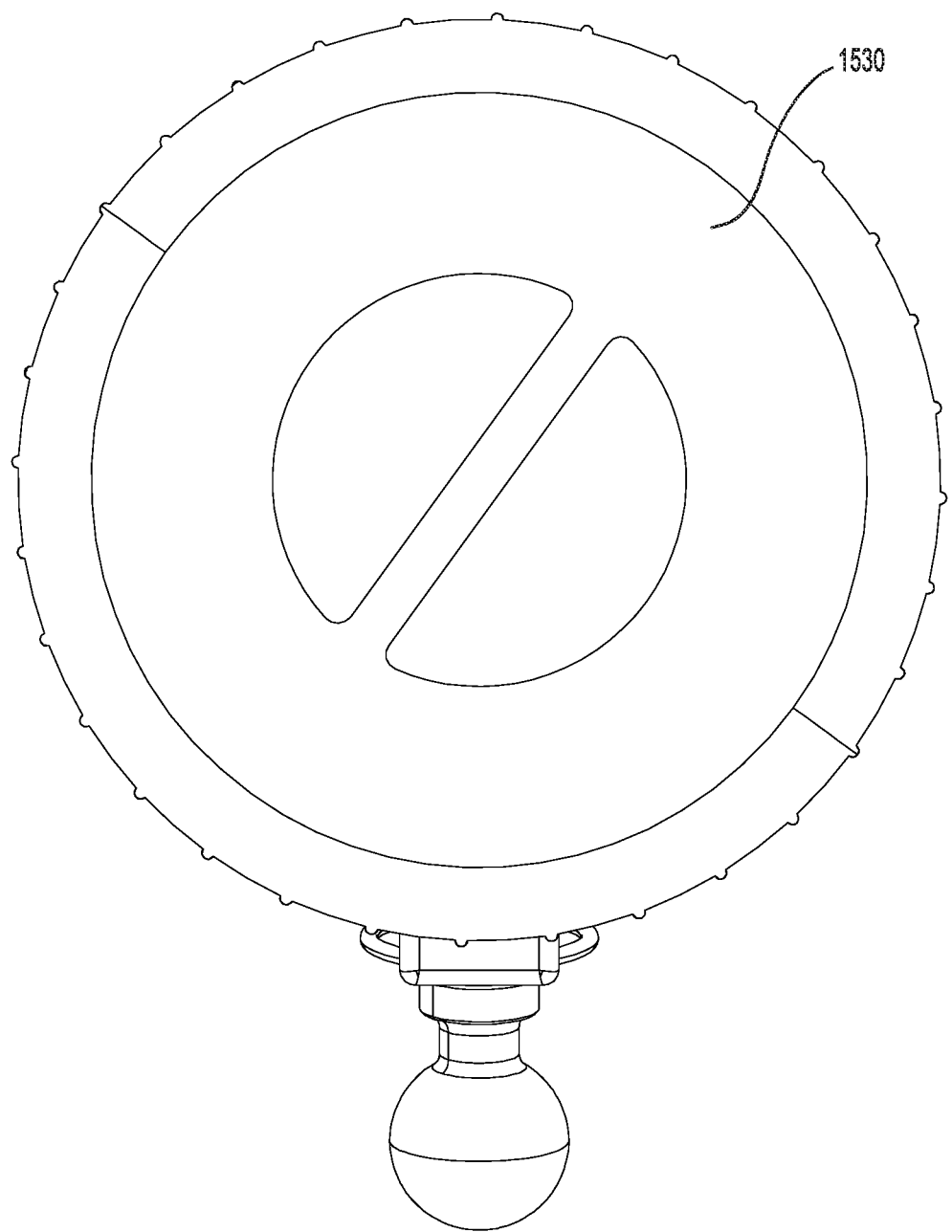
FIG. 15(D) is a portion of the device shown in FIG. 15(A).
Figure 15E:
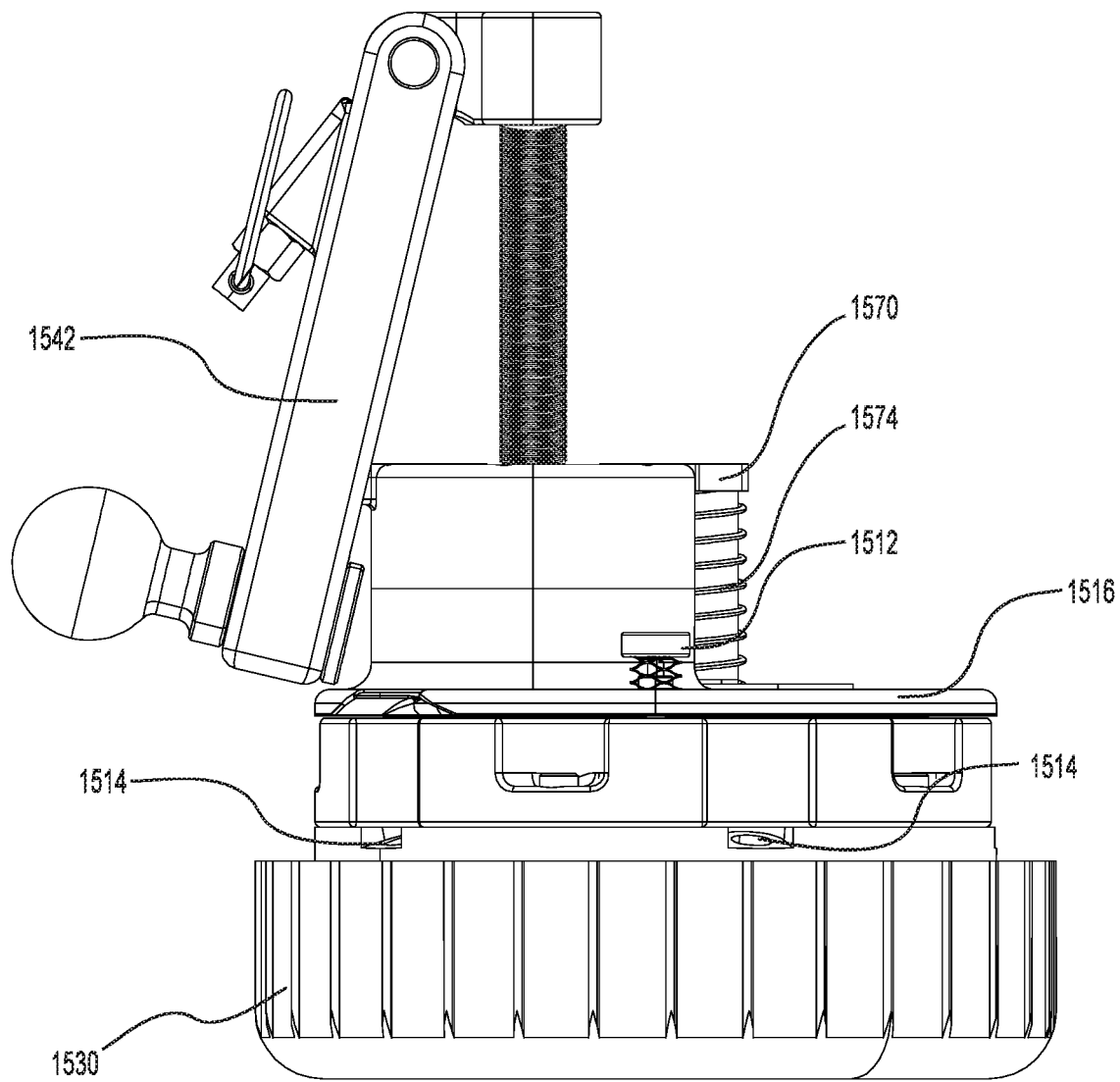
FIG. 15(E) is a first side view of the device shown in FIG. 15(A).
Figure 15F:
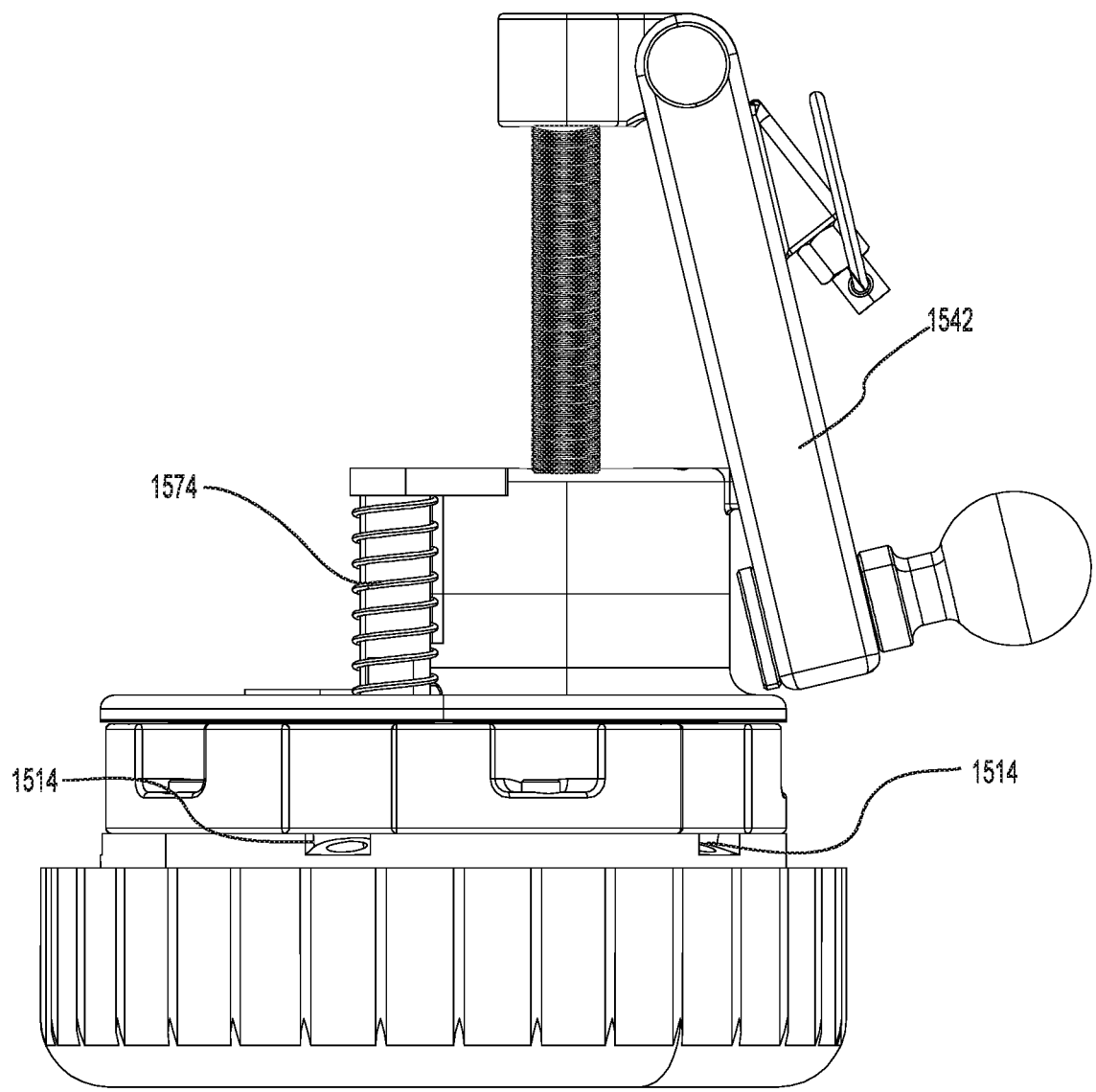
FIG. 15(F) is a second side view of the device shown in FIG. 15(A).
Figure 15G:
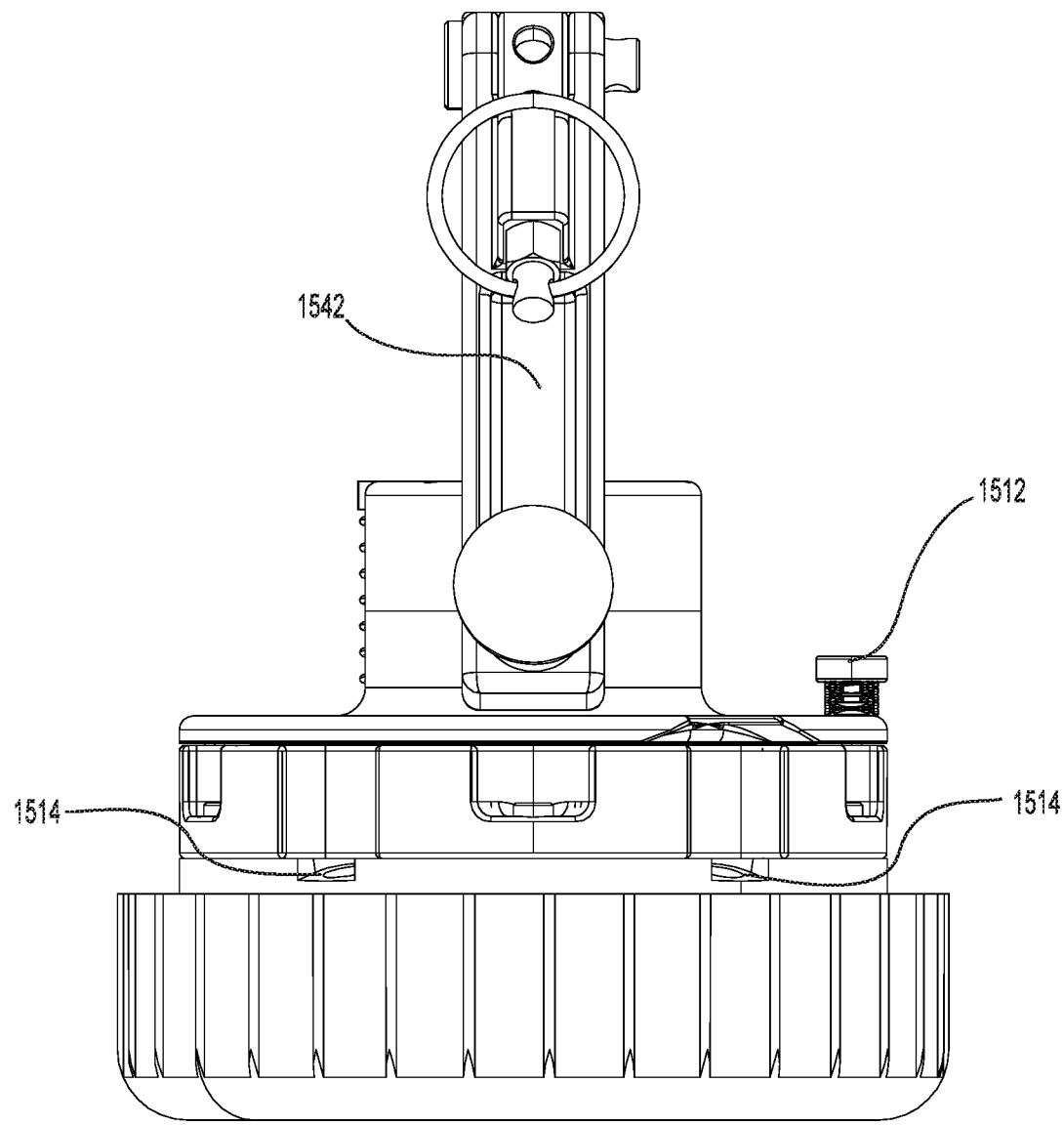
FIG. 15(G) is a front view of the device shown in FIG. 15(A).
Figure 15H:
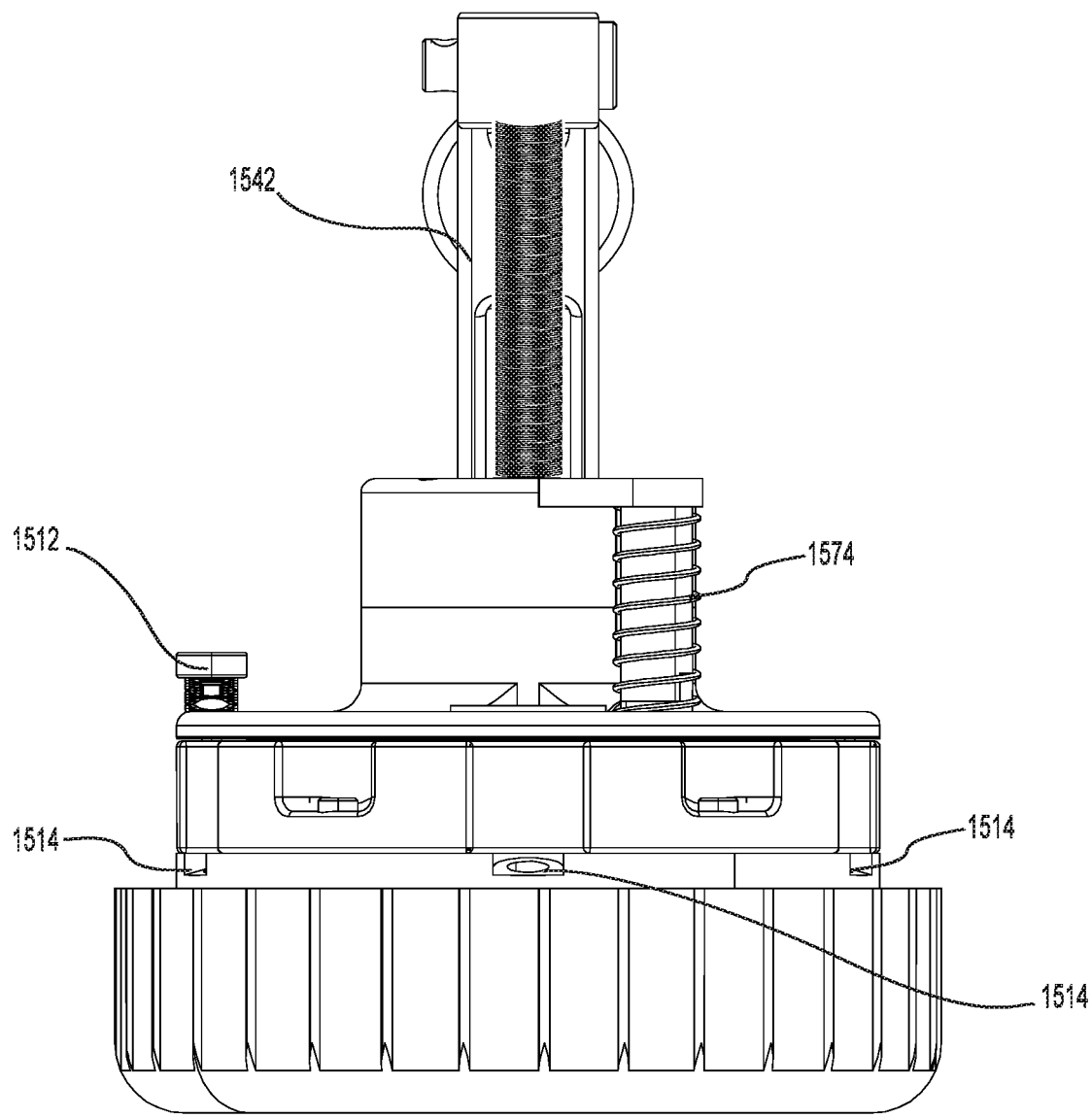
FIG. 15(H) is a rear view of the device shown in FIG. 15(A).
Figure 15I:
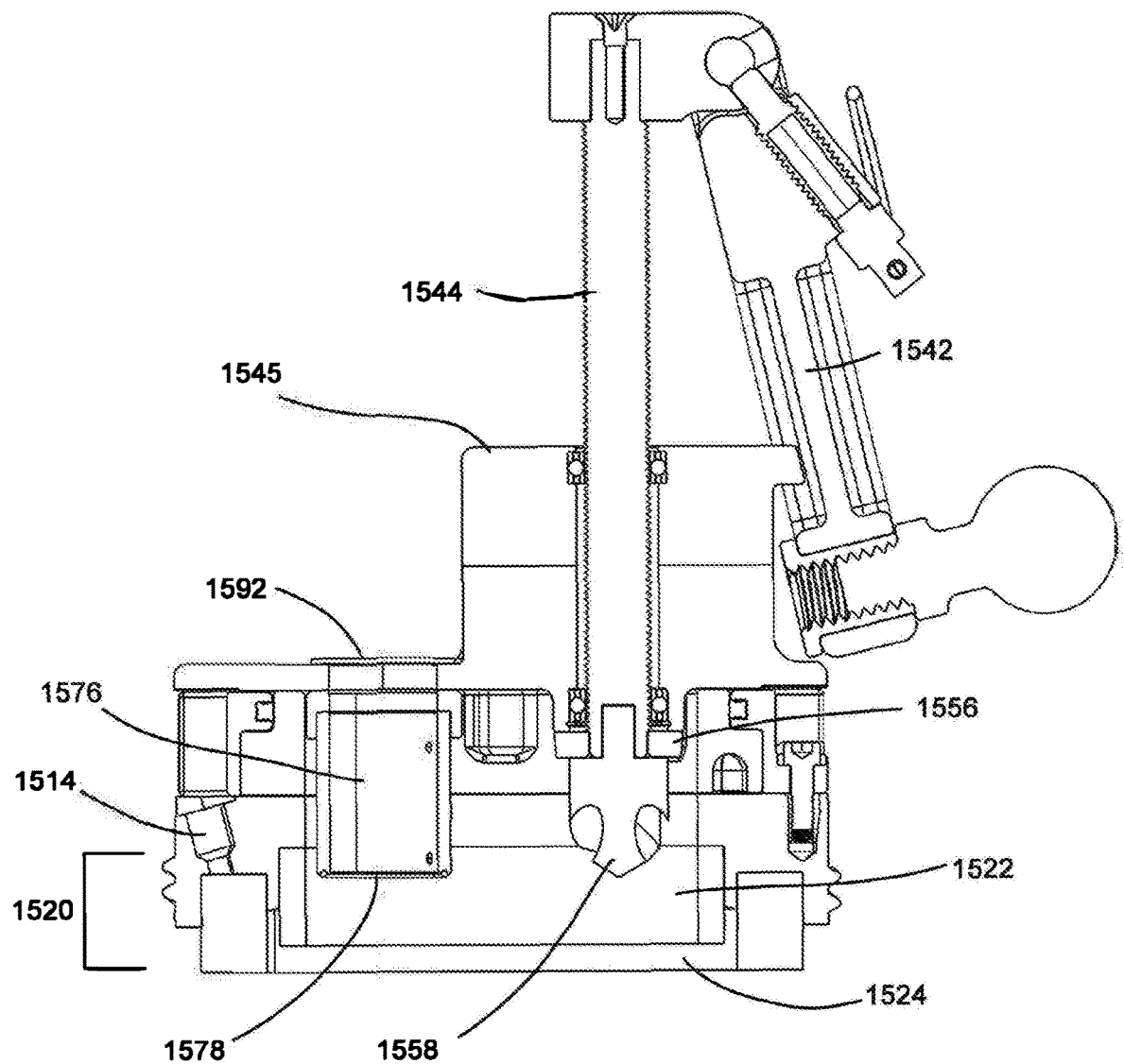
FIG. 15(I) is a partial cross-sectional view of the device shown in FIG. 15(A).

Referring to FIGS. 15(A)-15(J), in any embodiments housing 1510 of access device 1500 may include rotation control 1512 (shown in FIG. 15(C)), fastener holes 1514 (shown in FIG. 15(E)), lid 1516 (shown in FIG. 15(E)), adhesive and sealing element 1520 (shown in FIG. 15(I)), and cap 1530 (shown in FIG. 15(D)). Various components of access device 1500 may mount to housing 1510. Housing 1510 may facilitate providing at least a semi-sterile environment for diagnosis and/or treatment of intracranial pressure. For example, housing 1510 may at least partially seal a treatment area from an outside area and prevent contaminants (e.g., dust, debris, bacteria, etc.), from entering the treatment area. Housing 1510 may be constructed from a metal, a plastic, an alloy, a polymer, and/or any other material. In any embodiments, housing 1510 may be substantially cylindrical.

Referring specifically to embodiments of access device 1500 and FIG. 15(E), lid 1516 may mount components of access device 1500. In any embodiments, lid 1516 may be or include a top surface of housing 1510. In any embodiments, lid 1516 may facilitate positioning of the components of access device 1500 (e.g., drill 1540, cauterizer 1570, etc.). Lid 1516 may be rotatably coupled to a top portion of housing 1510. Rotation of lid 1516 may reposition components of access device 1500 coupled thereto. For example, while access device 1500 is coupled to a patient's head, lid 1516 may rotate freely of housing 1510 thereby facilitating aligning various components of access device 1500 with a treatment area. Thus, in at least one embodiment, in a first rotational orientation lid 1516 may position drill 1540 over an intended burr hole location, and in a second rotational orientation, lid 1516 may position cauterizer 1570 over the intended burr hole location. In any embodiments, cauterizer 1570 may be offset from the drill 1540.

In any embodiments, rotation control 1512 may control rotation of lid 1516. For example, a user may operate rotation control 1512 to facilitate locking and/or unlocking rotation of lid 1516. In some embodiments, rotation control 1516 is a button. For example, a user may press and hold rotation control 1512, rotate lid 1516, and release rotation control 1512 to lock lid 1516 into the new rotational orientation. In some embodiments, rotation control 1512 is spring-loaded. In any embodiments, rotation control 1512 may be self-locking. For example, rotation control 1512 may automatically lock rotation of lid 1516 when not depressed by a user. In any embodiments, lid 1516 may include access hole 1590. For example, lid 1516 may include one or more openings that facilitate user access to a treatment area contained by housing 1510. Thus, in at least one embodiment, a user may pass a needle through an opening in lid 1516 to collect fluid from a patient's head.

Referring now specifically to FIG. 15(D), cap 1530 is shown. Cap 1530 may cover a bottom of access device 1500. In any embodiments, cap 1530 may create at least a partial seal with the bottom of housing 1510. In any embodiments, cap 1530 may facilitate maintaining a sterilized condition of components of access device 1500 (e.g., drill 1540, etc.). In any embodiments, cap 1530 may protect adhesive and sealing element 1520 from contaminants. Additionally or alternatively, cap 1530 may prevent adhesive and sealing element 1520 from drying out, thereby improving a usability and/or longevity of the adhesive. Cap 1530 may be removable to expose adhesive and sealing element 1520 for application of access device 1500 to a patient's head. Thus, in some embodiments, cap 1530 is removably coupled (e.g., through friction and/or suction) to housing 1510. Cap 1530 may be constructed from plastic.

Attachment to Cranium (Fasteners)

In at least one embodiment, an intracranial access device as described herein includes an attachment mechanism, such as a plurality of fasteners, to securely position the device on the patient's head. Attachment mechanisms that rely on a connection to a scalp may be susceptible to becoming insecure when the scalp moves. Attachment mechanisms that involve attachment to the cranium (skull) itself have greater structural stability and are less prone to movement. For example, attachment of the device to the cranium, rather than the scalp, achieves a rigid fixation.

As shown in FIG. 1(A), in at least one embodiment, one or more fasteners 3 secure the device to the cranium itself. The fasteners may be, for example, cranial bone screws, selected to have a suitable size, thread type, thread pitch, self-tapping properties, and length. In some embodiments, the fasteners extend through the scalp to a depth that is about 2 mm into the outer table of the cranium. The fasteners may be inserted into the cranium manually or via externally powered tools. In some embodiments, the fasteners are housed within the housing and inserted into the cranium by a built-in electromechanical systems integrated into the device for automated insertion. As depicted in the figures and discussed below, the fastener 3 insertion sites are separate from the burr hole created by the drill of the device. In some embodiments, the fasteners 3 may be deployed after a first triggering of the device 1, such as when the lock button B2 is actuated. In some embodiments, the device 1 includes four, six, or more fasteners 3, generally arranged so as to surround the opening of the housing and/or generally distributed evenly around the circumference of the patient-facing side of the housing, as illustrated in the figures.

In some embodiments, each fastener 3 may be equipped with a plurality of hooks 4, such as barbs, which extend from lateral sides of the fastener 3. When present, the hooks 4 further assist with securing the fasteners 3, and hence the device, in place. As shown in FIG. 6, the housing 2 may have openings 15 to accommodate the hooks 4. The number of fasteners and openings and hooks shown is illustrative only; in some embodiments, an alternative number of openings 15 and hooks 3 may be present. As shown in FIG. 7, after fasteners 3 are inserted into the cranium, they may be pulled back slightly so as to compress the gasket 12 and provide a tight seal between the cranium and the device 1.

The device 1 is configured to be difficult to remove once the fasteners have been deployed, so as to help maintain the device securely in place and provide relatively aseptic conditions for the exposed part of the skull. Thus, once attached via the fasteners, the device 1 is configured to remain locked in place until removed, such as with a key mechanism (not shown) or surgically.

In any embodiments, fastener holes 1514 (e.g., as shown in FIG. 15(H), etc.) may receive fasteners such as bone screws to secure access device 1500 to a patient's head. In any embodiments, fastener holes 1514 may include an opening extending through housing 1510 that are configured to receive a bone screw. Housing 1510 may include a number of fastener holes 1514 distributed around an outside circumference of housing 1510.

Figure 15J:
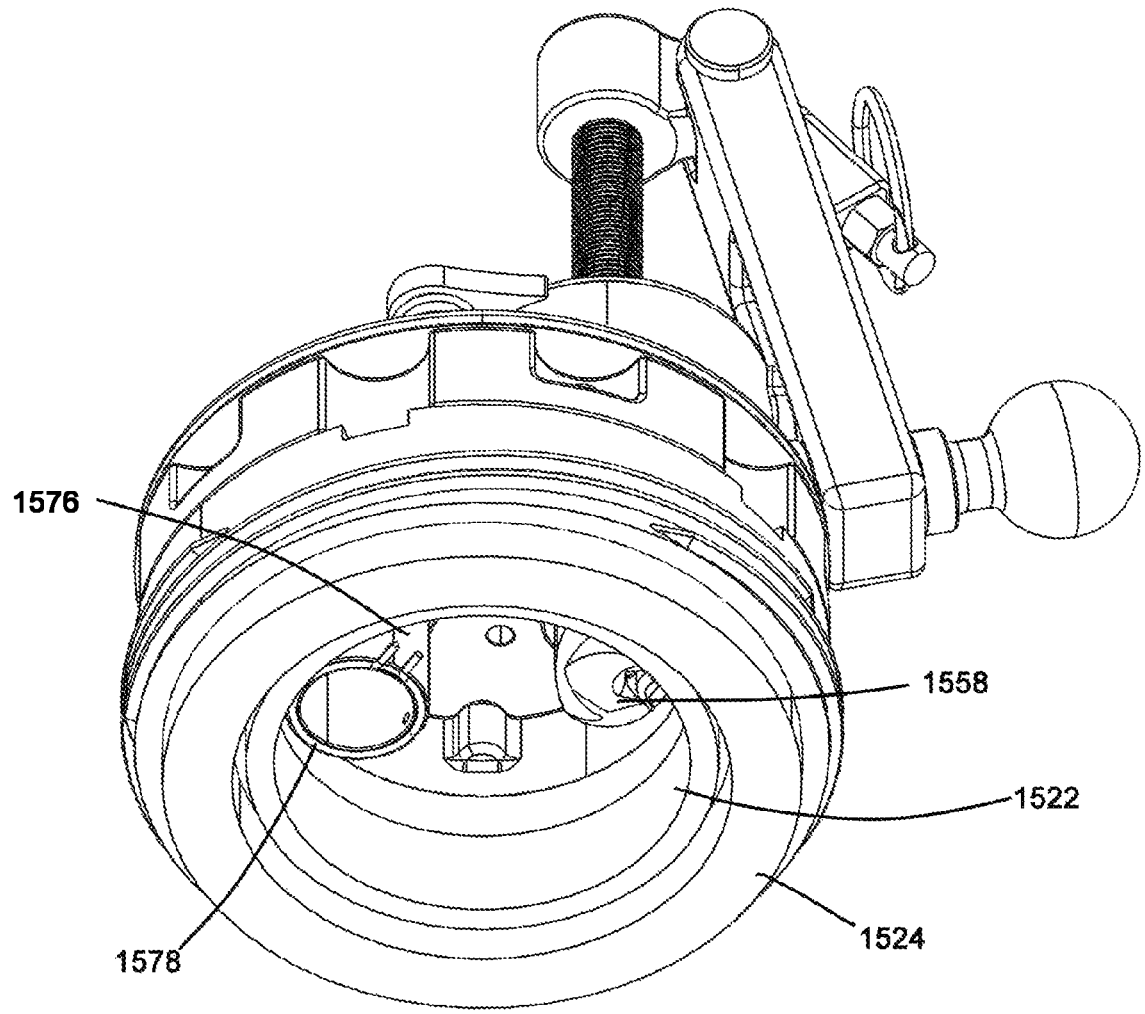
FIG. 15(J) is a bottom perspective view of the device shown in FIG. 15(A).

Additionally or alternatively, access device 1500 may be coupled to a patient's head via adhesive and sealing element 1520 (shown in FIGS. 15(I) and 15(J)). Adhesive and sealing element 1520 may include a first portion 1522 and a second portion 1524. First portion 1522 may be or include a closed-cell foam. For example, first portion 1522 may include a microcellular urethane foam. Second portion 1524 may be or include an open-cell foam. For example, second portion 1522 may include a polyurethane foam. In any embodiments, adhesive and sealing element 1520 may be substantially tubular. For example, adhesive and sealing element 1520 may be a hollow cylinder coupled to a bottom of housing 1510. In any embodiments, adhesive and sealing element 1520 may have a similar diameter as housing 1510.

Adhesive and sealing element 1520 may include an adhesive. For example, an adhesive including cyanoacrylate, such as Permabond® 799 made by Permabond LLC of Pottstown, PA, may be applied to first portion 1522 and/or second portion 1524 to facilitate coupling access device 1500 to a patient's head. In any embodiments, the adhesive may be a fast curing adhesive. In any embodiments, the adhesive may be held within second portion 1524. In any embodiments, the adhesive element may facilitate filling gaps in the open-cell foam thereby creating a seal around the treatment area. In any embodiments, first portion 1522 may be positioned concentrically within second portion 1524 (as shown in FIG. 15(J)). In any embodiments, first portion 1522 may at least partially seal the treatment area off from adhesive contained in second portion 1524 and/or an external environment. In any embodiments, adhesive and sealing element 1520 may include holes corresponding to fastener holes 1514 to facilitate driving a bone screw through adhesive and sealing element 1520 into a surface such as a patient's scalp.

Retractor with Retracting Blades

Figure 3A:
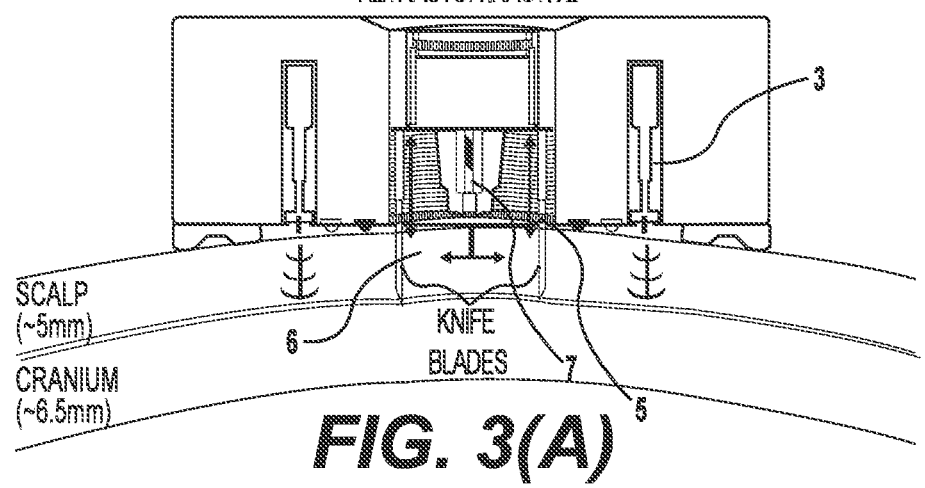
FIG. 3(A) is a lateral view of an intracranial access device including a retractor, as shown in an inactive state, according to at least one embodiment described herein.
Figure 3B:
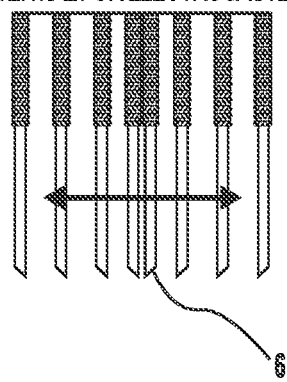
FIG. 3(B) is a lateral view of a retractor, according to at least one embodiment described herein.

According to at least one embodiment, intracranial device 1 is outfitted with a retractor 5 comprising at least one blade 6, as shown in FIG. 3(A), configured to cut into and retract the patient's scalp. A plurality of blades 6 may be provided which are structured to incise the scalp, optionally provide electrocautery to stop bleeding of the scalp (as discussed in more detail below), and then retract the scalp to expose the skull. FIG. 3(A) depicts the retractor 5 in an inactive state. The at least one blade 6 is configured to make a circular incision into the skin of a patient's scalp. In some embodiments, the retractor 5 includes, for example, at least two blades 6 disposed on opposite sides of drill 7, with each blade 6 being configured to move in a vertical direction relative to the housing, in an up (stowed) and down (deployed) manner into the patient. As shown in FIG. 3(B), the blades 6 may comprise a plurality of blades spaced adjacent to each other. The blades 6 are configured to incise the scalp. In some embodiments, the blades 6 are configured to travel through a drill bit 9 when drill bit 9 is in an open state.

Figure 3C:
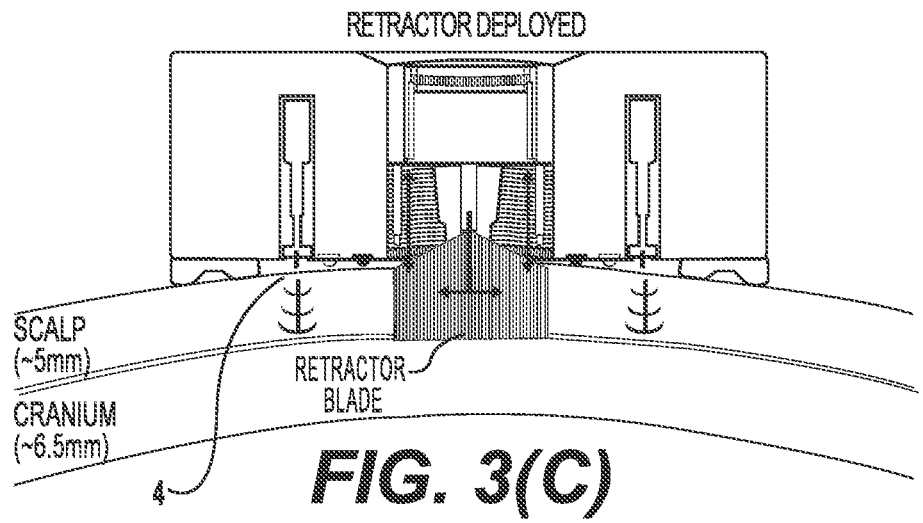
FIG. 3(C) is a lateral view of an intracranial access device including a retractor, as shown in an active state, according to at least one embodiment described herein.
Figure 3D:
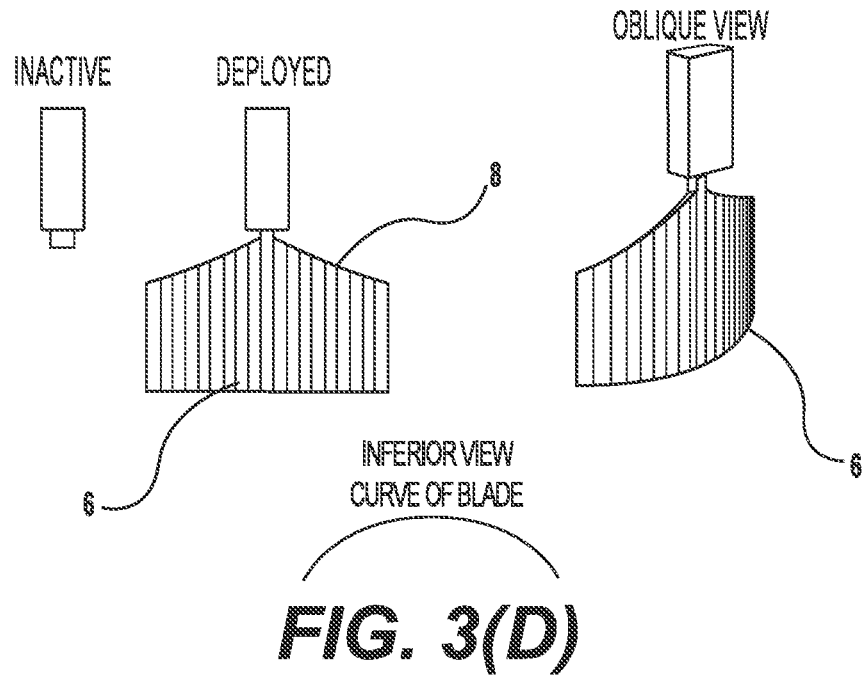
FIG. 3(D) depicts a retractor in an inactive state, in an active state, and in an active state in perspective and rear views, according to at least one embodiment described herein.

FIG. 3(C) depicts the retractor 5 in a deployed state. FIG. 3(D) depicts the retractor 5 in several states: an inactive, un-deployed (stowed) state; a deployed state as seen from a front view and in a perspective view, and further shows a bottom or inferior view of the curvature of the blade 6 in some embodiments. As seen in FIG. 3(C), in some embodiments, when the at least one blade 6 is inserted through the open drill 7, the at least one blade 6 may fan out laterally at a position beneath the drill 7, so as to cut into the patient's scalp. The at least one blade 6 may initially cut linearly, and then fan out into two semicircles to retract the cut skin against edges of the opening of housing 2 and out of the way. In some embodiments, the at least one blade 6 may be a high-speed alternating blade. In some embodiments, the blade 6 may be curved and comprise a plurality of spring-loaded panels 8. In some embodiments, the blade panels are configured to open once the at least one blade 6 is fully deployed (i.e., once fully delivered through the drill bit 9). In some embodiments, the configuration of the blade(s) 6, such as their position and curvature, may protect the skull from the drill 7 itself.

Drill Assembly

In at least one embodiment, an intracranial access device as described herein includes a hollow drill 7 housed in the opening of the housing, such as illustrated in FIGS. 1, 2 and 3(A)-3(B), for example, having a drill bit (i.e., drill head) 9. In other embodiments, a drill (and optionally retractor with retractor blades) is provided separately. The drill is actuated by rotation, and may have a telescoping motion mechanism to cause the drill to move in a linear path so as to control a depth of the drill relative to the cranium.

In some embodiments, the drill bit 9 has a closed position and an open position, wherein the drill bit is structured to penetrate the cranium in the closed position and allow passage of one or more objects or fluid through the drill bit in the open position. In some embodiments, the drill bit 9 has a circular base 9B from which the drill tips 9C project, as shown in FIGS. 2(A) and 2(C). As seen from the bottom in FIG. 2(B), when active drilling is underway, the drill bit is in a closed position such that tips 9C touch each other. On the other hand, as seen in FIGS. 2(C) and 2(D), when the drill is inactive, the drill bit is in an open position such that tips 9C are separated. When the drill bit is in an open position, objects or fluids can pass through passages 9A and the hollow drill 7, into or out of the cranium.

In some embodiments, the drill 7 may be deployed after a second triggering of the device 1, such as when the drill button B1 is actuated. In at least one embodiment, actuating the drill button B1 causes the drill to switch from an OFF state to an ON state. In some embodiments, in the ON state, the drill 7 deploys a telescoping member 10 to extend in an axial direction to guide the drill bit 9 closer to the skull.

Figure 8A:
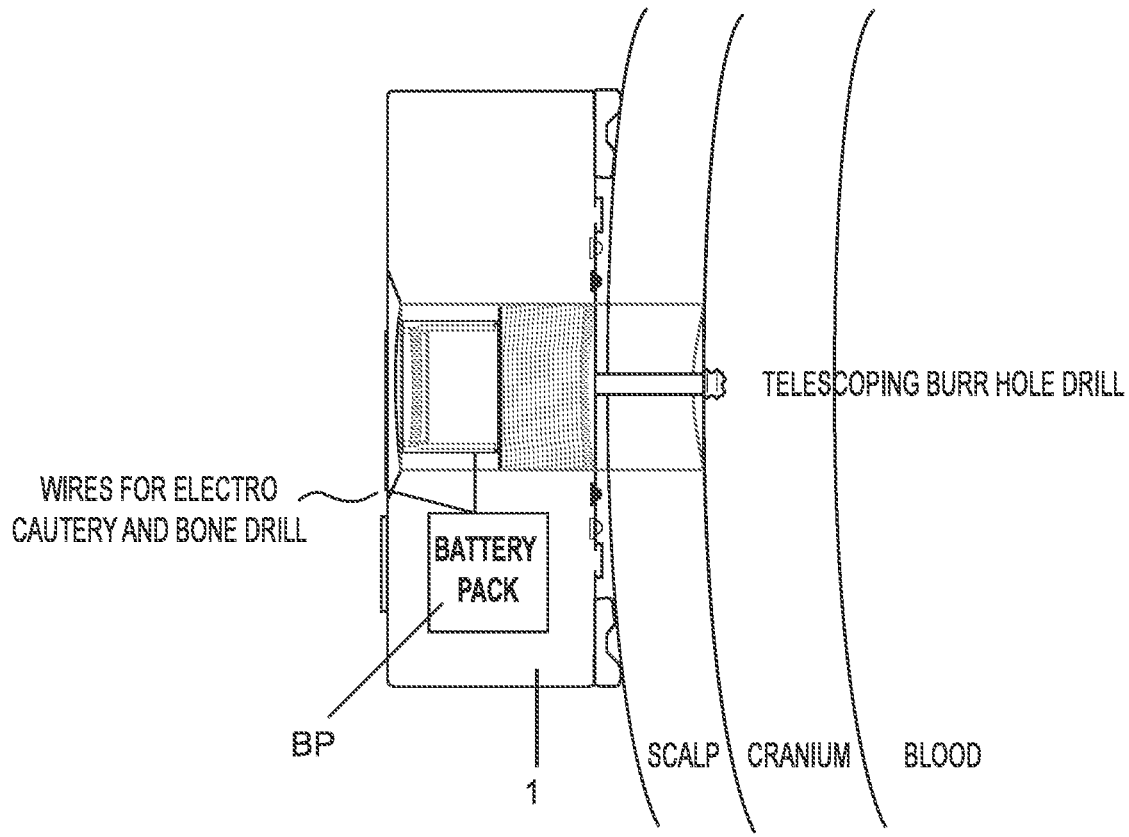
FIG. 8(A) depicts an intracranial access device as shown in a deployed state, according to at least one embodiment described herein.
Figure 8B:
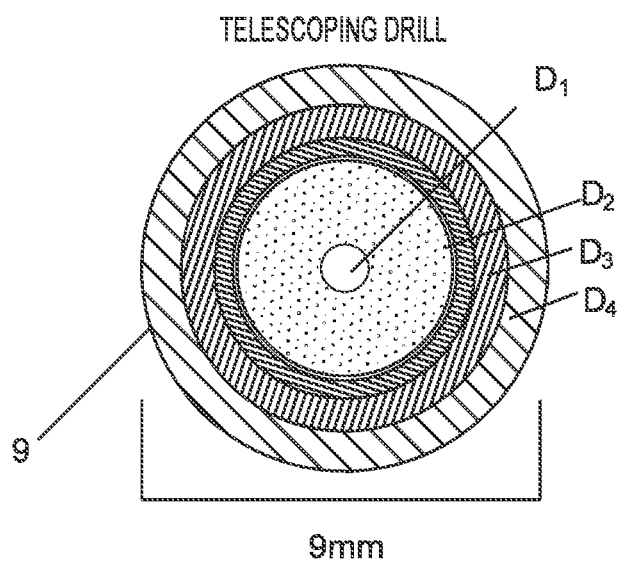
FIG. 8(B) is a cross-sectional view of a drill according to at least one embodiment described herein.
Figure 9:
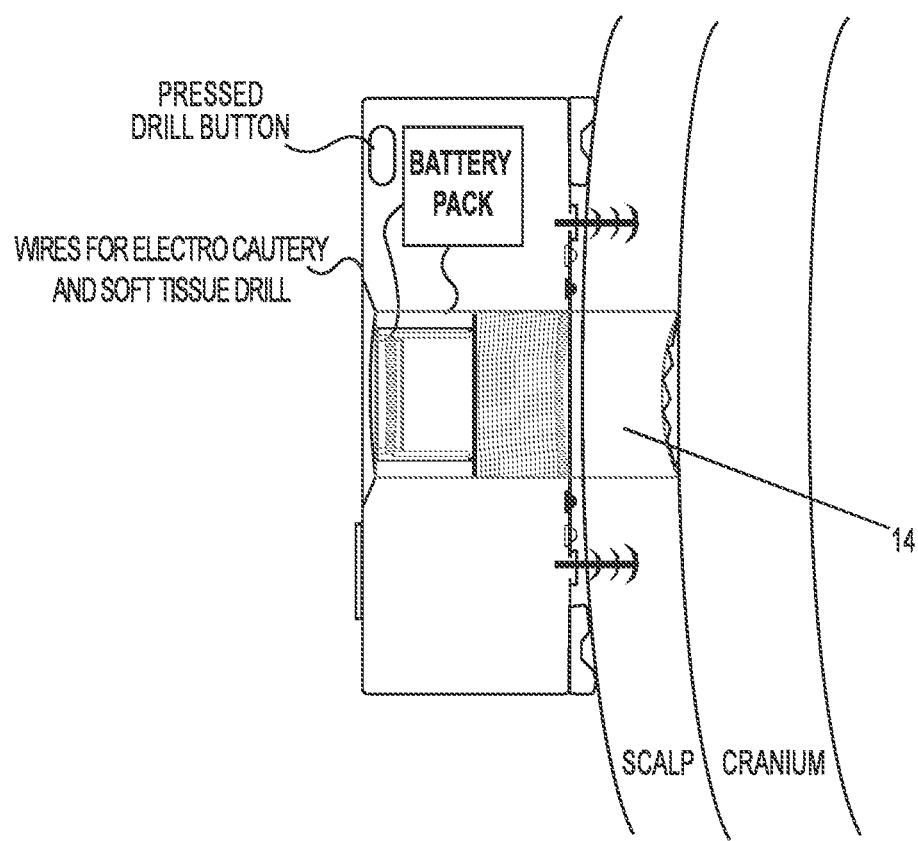
FIG. 9 is a side view of a drill according to at least one embodiment described herein.

As shown in in FIGS. 8(A)-8(B), in some embodiments the drill 9 may be a telescoping drill of approximately 9 mm in diameter, including a hollow core (shown as $D_1$) of about 3 mm in diameter. The drill 9 may include an inner segment (shown as $D_2$) having an inner diameter of about 6 mm and an outer diameter of about 7 mm, a middle segment (shown as $D_3$) having an inner diameter of about 7 mm and an outer diameter of about 8 mm, and an outer segment (shown as $D_4$) having an inner diameter of about 8 mm and an outer diameter of about 9 mm. In some embodiments, the drill 9 may telescope from about 1 cm (10 mm) in thickness, and may extend as far down as about 1.5 cm (15 mm) below a bottom edge of housing 2.

Figure 5A:
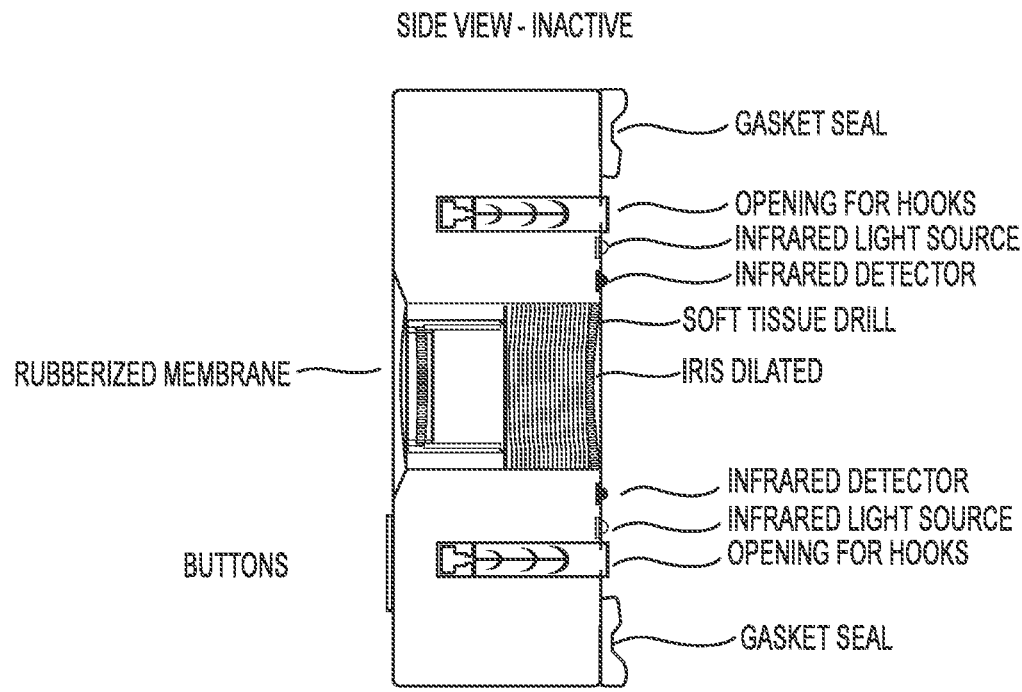
FIG. 5(A) depicts a side view of an intracranial access device in an inactive state, according to at least one embodiment described herein.
Figure 5B:
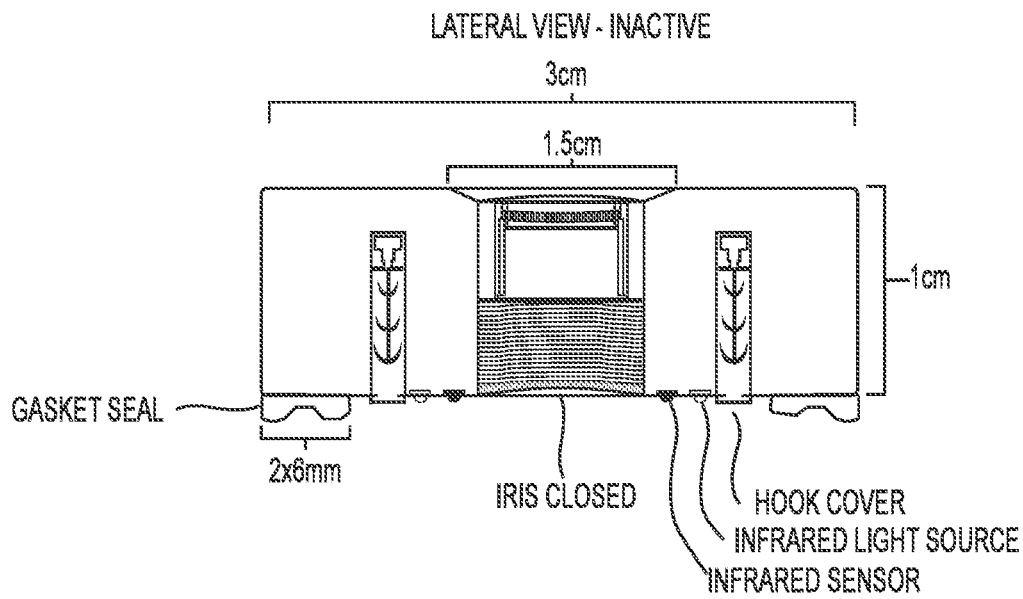
FIG. 5(B) depicts a further side view of an intracranial access device in an inactive state, according to at least one embodiment described herein.

In some embodiments, the telescoping member 10 of drill 9 includes a hollow barrel and a retractable/expandable cover member 14 at the patient-facing end of the barrel that is configured to close or open, alternatively, to permit direct access to the intracranial space. In some embodiments, the member 14, when in the closed position, covers the opening on the patient-facing side of the housing, as seen in FIGS. 5(A) and 5(B). In some embodiments, the member 14 may be formed similarly to an iris in that it dilates to its full opened position, providing access to the interior of the hollow drill and cranium, while preventing access when closed. For example, when the drill is activated, the member 14 may open, e.g., via an electromechanical actuator or via actuation of a biasing member such as a spring, in which the opening/closing of member 14 is controlled by releasing or engaging a catch of a spring-loaded mechanism.

Figure 10A:
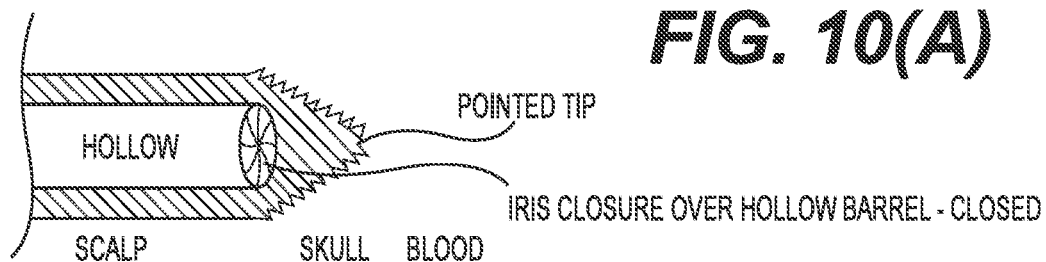
FIG. 10(A) is a side view of a drill in a first position, according to at least one embodiment described herein.
Figure 10B:
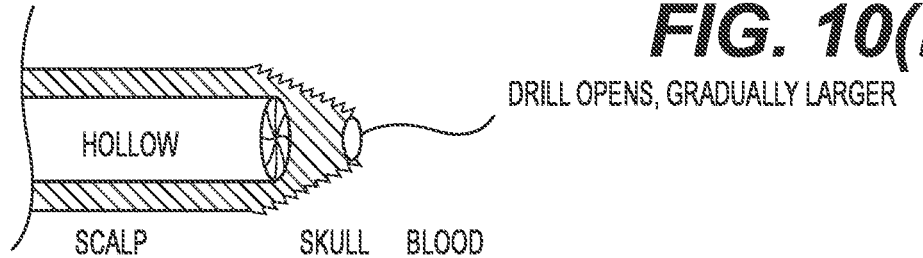
FIG. 10(B) is a side view of a drill in a second position, according to at least one embodiment described herein.
Figure 10C:
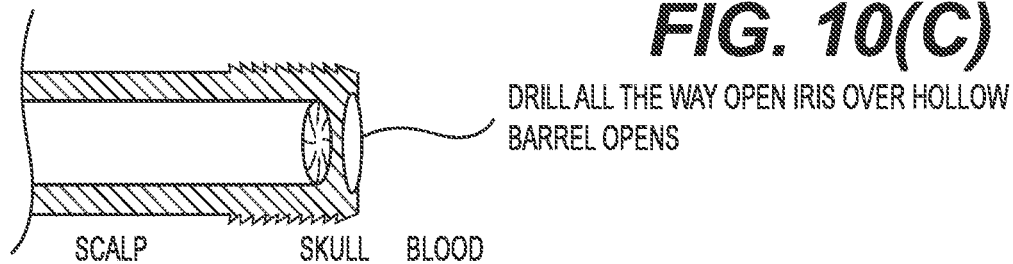
FIG. 10(C) is a side view of a drill in a third position, according to at least one embodiment described herein.
Figure 10D:
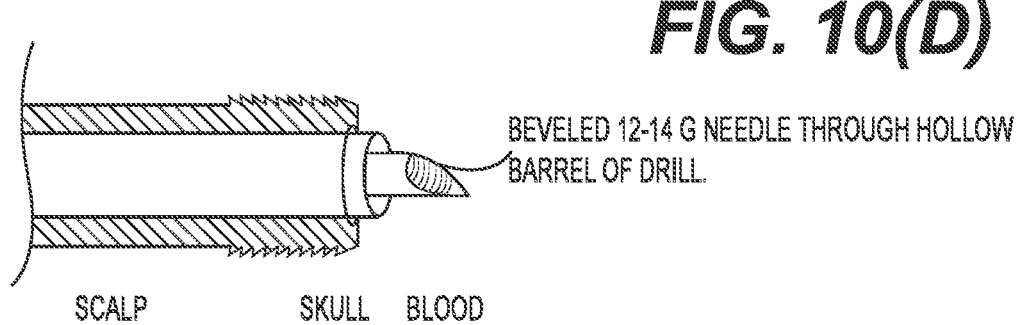
FIG. 10(D) is a side view of a drill in a fourth position, according to at least one embodiment described herein.

FIGS. 10(A)-10(D) depict the drill 7 in first through fourth positions described below. FIG. 10(A) depicts the drill in a first position, when it is being drilled through the cranium. The drill bit 9 is in a closed position with a pointed tip that is proximal to the skull, and the member 14 is in a closed state. FIG. 10(B) depicts the drill in a second position, where the drill bit 9 is partially opened. FIG. 10(C) depicts the drill in a third position, when the drill bit 9 is fully open, and the member 14 is in an opened state. FIG. 10(D) depicts the drill in an open state, with a needles (such as a size 12-14 gauge needle) inserted through the hollow barrel, open member 14 and open drill bit 9.

In some embodiments, the device may optionally further include one or more sensor or feedback-based control technologies to determine whether the cranium has been penetrated and/or a depth of penetration. In some embodiments, at least one sensor may be configured to detect a depth of the drill or a resistance encountered by the drill. For example, one or more resistance detectors may be incorporated into the drill bit 9. For example, a piezoelectric resistance sensor may be incorporated to detect a resistance level. The sensor may be positioned on the drill bit 9, e.g., on the end of the drill bit 9 and determine a depth of penetration by the drill bit 9, e.g., based on the resistance level.

In some embodiments, the sensing result may be communicated to an operator automatically. Further, in some embodiments, when the detection result indicates that a threshold depth or resistance level is met, the drill bit 9 may be controlled to cease drilling automatically. For example, when the resistance level is below a threshold, indicating that the drill bit 9 is encountering a relatively low resistance, the drill bit 9 may be stopped because the low resistance indicates that the cranium has been fully penetrated.

Additionally or alternatively, in some embodiments the drill may be limited to a fixed depth through the cranium so as to reduce the risk of over-penetration, such as by limiting the action of telescoping mechanism 10. In some embodiments, movement of the drill in the axial direction (i.e., a vertical direction with respect to the cranium) into the cranium ceases automatically when a specific event occurs, such as once the hemorrhage is detected at drill bit 9 or once the drill bit 9 it reaches a maximum depth. In such embodiments, the maximum depth may be set at about 2 cm. The maximum depth may be set to about 2 cm due to the average thickness of the human scalp being about 8 cm and the average thickness of the skull being about 7 mm. In such embodiments, a depth sensor and/or resistance sensor may be omitted.

In some embodiments, when drill bit 9 reaches a maximum depth, LEDs, such as the LEDS L1-L3, may flash to signal that the maximum penetration has been reached. Alternatively, a message may be displayed on a monitor in communication with the device 1. The monitor may display information such as a depth required to penetrate the skull and reach the hemorrhage for the operator's use in drainage.

Referring now specifically to FIG. 15(I), drill 1540 may include handle 1542, shaft 1544, and drill bit 1558. Shaft 1544 may couple to handle 1542, and/or drill bit 1558. In any embodiments, drill 1540 may be coupled to lid 1516. Handle 1542 may be usable to rotate and/or axially translate shaft 1544 thereby causing rotary motion of shaft 1544, advancement, and/or retraction of drill bit 1558. In some embodiments, handle 1542 is coupled to shaft 1544 via a pivot member to facilitate collapsible storage of handle 1542 when not in use. Drill bit 1558 may be coupled to an end of shaft 1544 and rotate with shaft 1544.

Hard stop washer 1556 may prevent over penetration of drill 1540. In any embodiments, hard stop washer 1556 may physically prevent further downward axial motion (e.g., towards a patient's head) beyond a threshold. For example, hard stop washer 1556 may prevent drill bit 1558 from penetrating deeper than about 11.5 mm at the center of drill bit 1558 and/or about 8.8 mm at an outer edge of drill bit 1558 into a patient's head. In any embodiments, the sides of hard stop washer 1556 may be angled to facilitate separate soft tissue from drill 1540. In any embodiments, drill 1540 may be operated manually (e.g., by manual rotation of handle 1542). Additionally or alternatively, operation of drill 1540 may be at least partially automated (e.g., through electronic control, via motor rotation of shaft 1544, etc.). Drill bit 1558 is configured to drill through tissue. For example, drill bit 1558 may be configured to penetrate through skin and/or bone. In any embodiments, drill bit 1558 may be made of metal or other suitable material. In any embodiments, drill bit 1558 is similar to drill bit 9 in at least some aspects noted above.

Cauterization

In at least one embodiment, the device 1 may further comprise an electro cauterization device (an electro-cauterizer) configured to cauterize the hole cut into the scalp and/or cranium to control bleeding. For example, an electro cauterization device may be deployed in conjunction with retractor 5, such that when blood flows from the incisions formed by the blade(s) 6 of retractor 5, an electrocautery procedure may be carried out to stop or lessen the blood flow. As noted above, the blade(s) 6 may be configured to provide electro cauterization. Additionally or alternatively, an electro cauterization device may be deployed in conjunction with drill 7, to stop or lessen local bleeding when the drill 7 drills through the cranium. In any embodiments, the electro cauterization device may be powered by a power supply in the device 1 or by an external power supply. Additionally or alternatively, the operator may take measures during cutting or drilling to lessen or localize bleeding. For example, the operator may clamp a superficial temporal artery in the temporalis muscle if severed to lessen bleeding.

In various embodiments, cauterizer 1570 (shown in FIG. 15(I)) is similar in at least some aspects to the electro cauterization device described above. In any embodiments, cauterizer 1570 may be coupled to lid 1516. In some embodiments, cauterizer 1570 is coupled to lid so as to be offset 180° from drill 1540. Cauterizer 1570 may include electrical connectors 1572 (shown in FIG. 15C), plunger 1574, tube 1576, and heating element 1578. Cauterizer 1570 may facilitate cauterization of a treatment area before and/or after creation of a burr hole. In any embodiments, cauterizer 1570 may be an electro cauterizer. For example, access device 1500 may include or be provided with a battery or other electrical energy storage device configured to provide electricity to cauterizer 1570 via electrical connectors 1572. In any embodiments, electrical connectors 1572 may facilitate connecting a power source. Plunger 1574 may be a spring-loaded mechanism for operating cauterizer 1570. For example, a user may depress plunger 1574 to cause heating element 1578 to lower to contact a treatment surface, thereby cauterizing the treatment surface.

In any embodiments, plunger 1574 may be offset from access hole 1590. For example, plunger 1574 may be axially offset from access hole 1590. Tube 1576 of cauterizer 1570 is a tube axially aligned with access hole 1590. In any embodiments, tube 1576 may be a ceramic tube. In any embodiments, tube 1576 may be hollow. Tube 1576 may facilitate access through an opening from access hole 1590 to the treatment area. In any embodiments, heating element 1578 may be coupled to an end of tube 1576. Heating element 1578 may be configured to generate heat upon application of electrical current. In any embodiments, heating element 1578 may be or include nichrome wire. In any embodiments, heating element 1578 may substantially circular in shape. For example, heating element 1578 may be shaped similarly as an end of tube 1576.

Sealing Members

In at least one embodiment, an intracranial access device as described herein includes members for sealing the device to the surface of the patient's head so as to provide a barrier between an interior of the housing 2 and the external environment. The intracranial access device as shown in FIG. 4, for example, includes a gasket 12 which is configured to affix the device to the surface of the head of a patient and a sealing membrane R (e.g., a sealing member) which is configured to cover the opening in the housing 2 on the operator-facing side. As shown in FIGS. 5(A) and 5(B), the gasket 12 seals edges of the housing to the surface of the patient's head, while the membrane R protects the opening in the housing 2. FIG. 6 is a bottom view of the housing 2 in which the gasket 12 is shown at an outermost periphery of the housing 2. The gasket 12 and sealing membrane R are designed to create a barrier to isolate a portion of the head of the patient from the external environment and lower the risk of infection by preventing ingress of contamination.

The gasket 12 may be a shape-compliant gasket which conforms in curvature to a portion of a patient's head. For example, the gasket 12 may comprise a pneumatic dam and may further employ adhesive material. In some embodiments, the gasket 12 may comprise a member configured to secrete a pharmaceutical agent, such as an antimicrobial agent, when compressed, so as to deliver pharmaceutical agent or drug to the site to thereby reduce the risk of infection.

The sealing membrane R is configured to provide a barrier between the interior of the opening of the housing and the exterior environment. The sealing membrane R may be an anti-microbial sealing membrane formed of a rubberized material, for example. The membrane R is configured to allow a needle or similar device (including a needle connected to a syringe) to penetrate through the membrane R. In some embodiments, the membrane R may seal around a needle penetrated through the membrane R. Thus, in some embodiments, the membrane R allows an operator to drain blood (e.g., epidural or subdural blood) one or more times using a needle, as discussed further below, while reducing the risk of an infection by preserving the area as aseptic or nearly aseptic.

In some embodiments, one or more of the blades 6 and membrane R are designed for single use and replaced after use on a given patient, but other components of device 1 are capable of being sterilized and reusable.

As discussed above, access device 1500 may be coupled to a patient's head via adhesive and sealing element 1520, embodiments of which are discussed above.

IR Sensors for Visualization and Localization of Intracranial Pathology and a Detection Device According to at least one embodiment, intracranial access device 1 is further equipped with a plurality of sensors configured to visualize and localize intracranial pathology, such as a hemorrhage location.

As shown in FIG. 6, the device 1 is further equipped with a plurality of infrared (IR) sensors 11 disposed at positions around the patient-facing side of the housing 2, configured to localize hemorrhage sites. The IR sensors 11 may be disposed circumferentially around the perimeter of the housing 2, such as between a periphery of housing 2 and the opening in the housing. A plurality of IR light sources 13 are positioned circumferentially around the perimeter of the housing 2, and may be disposed at intervals between IR sensors 11, such that IR sensors 11 and IR light sources 13 are provided in an alternating fashion.

Acute EDH and SDH are examples of intracranial pathologies that may be visualized and localized using sensors such as IR sensors. For example, near infrared spectroscopy (NIRs) may be used for non-invasive detection of EDH and SDH. Detection may be carried out using frequency-domain (FD) NIRs and/or time domain (TD) NIRS. Utilizing principles of both FD and TD NIRS, an absolute measure of scattering and absorption may be obtained, which allows for discriminating between materials such as bone, blood, and tissue. More specifically, FD and TD NIRS approaches allow for distinguishing among bone, blood and tissue due to the unique absorption and scattering properties of these materials. FD and TD NIRS principles may be used for detecting relatively large EDH and SDH.

More particularly, in accordance with some embodiments, an optical measurement system may be used to detect and localize the presence of a hemorrhage. For example, a single-channel optical system may be used to generally identify the location of a hemorrhage, whereas a multi-channel optical system may allow for a measurement of a total hemorrhage size in three dimensions. For example, a multi-channel optical system may be used to image an area of about 9 $cm^2$ with a resolution of 1 cm or less. Based on information gleaned from such systems, the presence of a hemorrhage may be determined, along with estimates of the location and size of the hemorrhage.

In some embodiments, infrared sensing may be implemented using techniques as described above, and/or known techniques including absorbance, reflection, scattering using continuous waves, pulsed 10-1000 Hz NIR, multispectral NIR at wavelengths ranging from 750 to 1050 nm, or combinations thereof. An optical system may include both IR light sources and IR sensors. In addition, software algorithms may be employed to detect the presence or absence of epidural and subdural blood in the intracranial space underlying the site of device 1. Such IR technologies may also be used to detect the proximity of the drill to a hemorrhage, so as to indicate when drilling should cease. In some embodiments, the IR sensors are incorporated into a separate device other than the intracranial access device 1. In some embodiments, the IR sensors are integrated into the device 1.

Figure 17A:
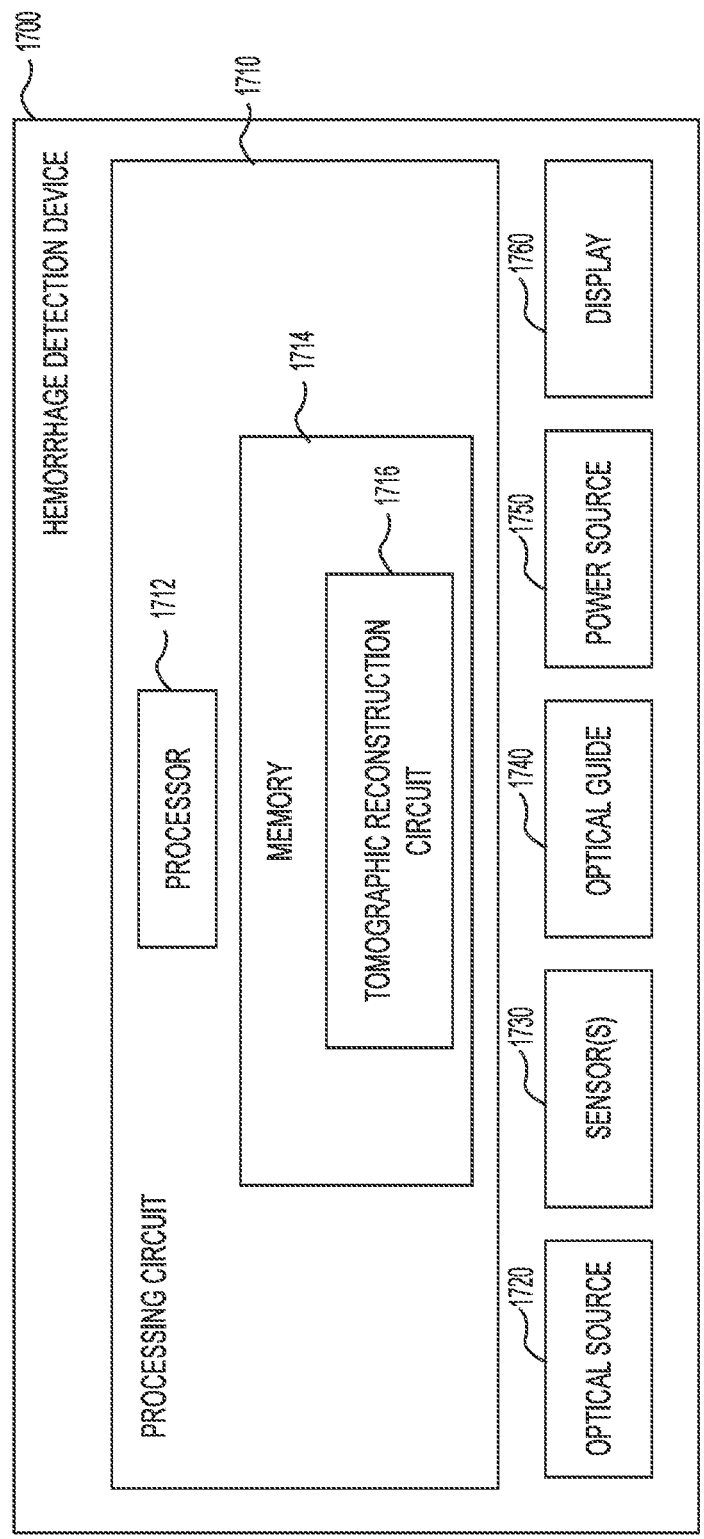
FIG. 17(A) is a block diagram of a hemorrhage detection device, according to at least one exemplary embodiment.
Figure 17B:
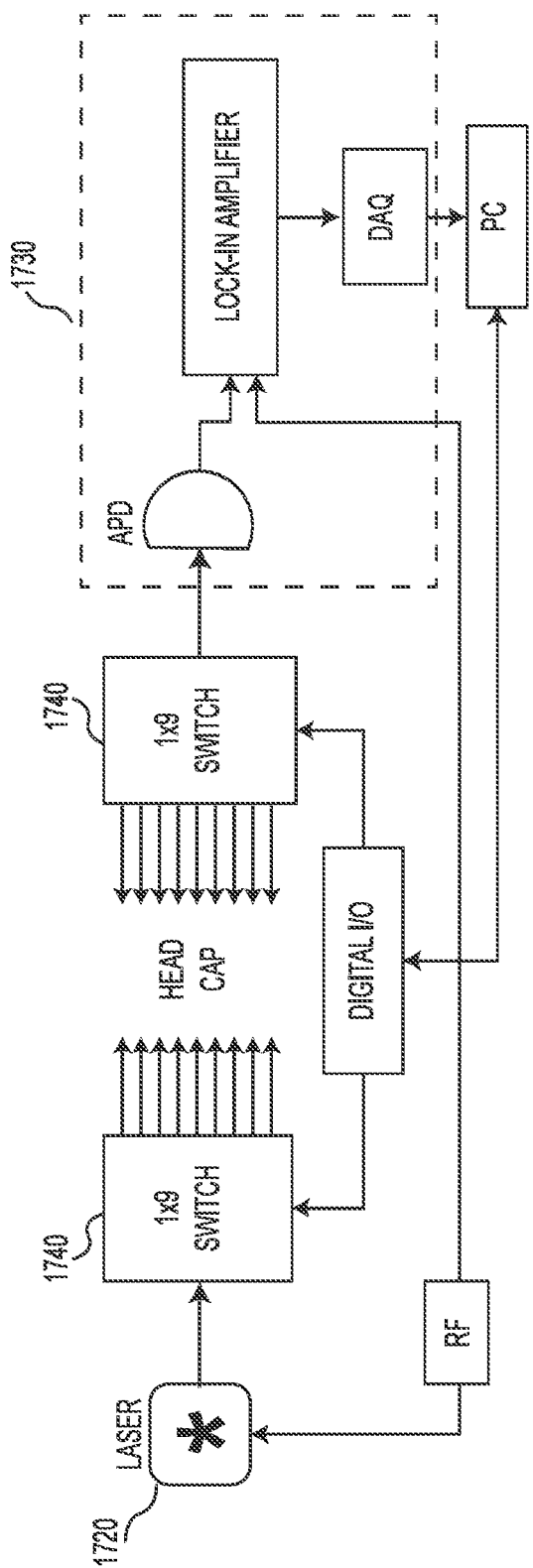
FIG. 17(B) is a block diagram of another hemorrhage detection device, according to at least one exemplary embodiment.

Referring now to FIGS. 17(A)-(B), in some embodiments, visualization and localization of intracranial pathology is facilitated by a separate hemorrhage detection device, shown as detection device 1700, according to an exemplary embodiment. Detection device 1700 may be used as a standalone device, separate of access device 1500. Additionally or alternatively, detection device 1700 may be used with access device 1500 and/or intracranial access device 1. For example, detection device 1700 may be used to identify and locate a hematoma, and access device 1 or access device 1500 may be used to access and/or treat the hematoma. In any embodiments, detection device 1700 may facilitate field-based identification, localization, and/or treatment of EDH and/or SDH. In any embodiments, detection device 1700 may utilize frequency-domain diffuse optical tomography (FD-DOT) to detect EDH and/or SDH by measuring optical scatter and/or absorption of light into tissue. In some embodiments, detection device 1700 is easily portable. For example, detection device 1700 may be or include a portable handheld device.

Turning specifically to FIG. 17(A), detection device 1700 typically may include processing circuit 1710, optical source 1720, sensor(s) 1730, optical guide 1740, and power source 1750. Processing circuit 1710 may include processor 1712 and memory 1714. Memory 1714 typically may have instructions stored thereon that, when executed by processor 1712, cause processing circuit 1710 to perform the various operations described herein.

The operations described herein may be implemented using software, hardware, or a combination thereof. Processor 1712 may include a microprocessor, ASIC, FPGA, etc., or combinations thereof. In any implementations, processor 1712 may be a multi-core processor or an array of processors. Memory 1714 may include, but is not limited to, electronic, optical, magnetic, or any other storage devices capable of providing processor 1712 with program instructions. Memory 1714 may include a floppy disk, CD-ROM, DVD, magnetic disk, memory chip, ROM, RAM, EEPROM, EPROM, flash memory, optical media, or any other suitable memory from which processor 1712 can read instructions. The instructions may include code from any suitable computer programming language such as, but not limited to, C, C++, C#, Java, JavaScript, Perl, HTML, XML, Python and Visual Basic.

Memory 1714 typically may include tomographic reconstruction circuit 1716. Tomographic reconstruction circuit 1716 may receive amplitude and/or phase information from sensor(s) 1730 associated with light transmitted into tissue by optical source 1720 and analyze the amplitude and/or phase information to detect and/or locate hemorrhages using tomographic reconstruction. In various embodiments, tomographic reconstruction circuit 1716 identifies hemorrhaging based on a change in the amplitude and/or phase of hemorrhage tissue as compared with non-hemorrhage tissue. For example, healthy tissue (e.g., tissue not containing a hemorrhage, etc.) may have a first set of amplitude and/or phase delay characteristics and tissue having a hemorrhage may have a second set of amplitude and/or phase delay characteristics that facilitate detection thereof by tomographic reconstruction circuit 1716. In any embodiments, tomographic reconstruction circuit 1716 may determine an amplitude of light received by sensor(s) 1730 corresponding to the light transmitted into tissue by optical source 1720 for healthy tissue and compares the amplitude to information received by sensor(s) 1730 to identify a hemorrhage.

Additionally or alternatively, tomographic reconstruction circuit 1716 may determine a phase of light received by sensor(s) 1730 corresponding to the light transmitted into tissue by optical source 1720 for healthy tissue and may compare the phase to information received by sensor(s) 1730 to identify a hemorrhage. In some embodiments, tomographic reconstruction circuit 1716 optionally generates a baseline absorption associated with tissue (e.g., healthy tissue and/or tissue containing a hemorrhage, etc.) based on an intensity of reflected/diffused light generated by optical source 1720. Additionally or alternatively, tomographic reconstruction circuit 1716 may optionally generate a baseline phase shift associated with tissue (e.g., healthy tissue and/or tissue containing a hemorrhage, etc.) based on an intensity of reflected/diffused light generated by optical source 1720. In some embodiments, tomographic reconstruction circuit 1716 may optionally determine a threshold amount of absorption below the baseline that indicates the presence of a hemorrhage.

Additionally or alternatively, tomographic reconstruction circuit 1716 may optionally determine a threshold amount of phase shift away from the baseline that indicates the presence of a hemorrhage. In some embodiments, tomographic reconstruction circuit 1716 generates a sensitivity matrix based on a model of light flux through the tissue under measurement. In some embodiments, tomographic reconstruction circuit 1716 generates a three-dimensional map of absorption values that models the three-dimensional (x, y and z) volume that produced the measured values. In any embodiments, tomographic reconstruction circuit 1716 may track a position of a hemorrhage on a patient's head. For example, tomographic reconstruction circuit 1716 may track a lateral, horizontal, and/or vertical position of an identified hemorrhage.

In any embodiments, tomographic reconstruction circuit 1716 may facilitate three-dimensional localization of hemorrhages. Additionally or alternatively, tomographic reconstruction circuit 1716 may facilitate size estimation of detected hemorrhages. In any embodiments, tomographic reconstruction circuit 1716 may employ a frequency domain (FD) detection scheme. Additionally or alternatively, tomographic reconstruction circuit 1716 may employ a continuous wave (CW) and/or a time domain (TD) detection scheme.

Optical source 1720 may be a source of near-infrared light in some embodiments. For example, optical source 1720 may be a source of 690 nm wavelength light. In some embodiments, optical source 1720 includes a laser and/or may be a source of non-NIR light. For example, optical source 1720 may include a gas laser, a solid-state laser, a fiber laser, a photonic crystal laser, a semiconductor laser, a dye laser, a free-electron laser, and/or an exotic media laser. In any embodiments, optical source 1720 may generate amplitude modulated light. For example, optical source 1720 may generate light having a 50 MHz sinusoidal intensity modulation frequency that may facilitate FD-DOT measurement and/or analysis. Additionally or alternatively, optical source 1720 may generate continuous wave (CW) light. In any embodiments, optical source 1720 may transmit light into tissue. For example, optical source 1720 may be positioned to transmit light into the head of a patient. In any embodiments, light from optical source 1720 may penetrate several centimeters (e.g., about 2 cm, about 3 cm, or about 3.5 cm) into tissue. In any embodiments, optical source 1720 may include an oscillator. For example, optical source 1720 may include an oscillator configured to modulate an amplitude of injected light.

Sensor(s) 1730 typically measures light produced by optical source 1720 as it diffuses through tissue. In any embodiments, sensor(s) 1730 are positioned offset from optical source 1720 and/or a transmission element (a transmitter) of optical source 1720 (e.g., an output of optical guide 1740, etc.). For example, sensor(s) 1730 may be offset a fixed distance (e.g., 20 mm, etc.) from optical source 1720 and/or a transmission element of optical source 1720 and/or may be offset a dynamic distance from optical source 1720 and/or a transmission element of optical source 1720. In any embodiments, sensor(s) 1730 may be paired with one or more optical sources 1720. For example, a number of optical sources 1720 may be paired with corresponding sensor(s) 1730 in a known configuration (e.g., multi-channel measurements).

Additionally or alternatively, sensor(s) 1730 may be arranged with a single optical source 1720 (e.g., single-channel measurements). In various embodiments, sensor(s) 1730 include light sensors (e.g., photodetectors). For example, sensor(s) 1730 may include photoelectric devices, semiconductor photodetectors, photovoltaic photodetectors, thermal photodetectors, photochemical photodetectors, polarization photodetectors, and/or graphene and/or silicon photodetectors. In some embodiments, sensors(s) 1730 include an avalanche photodiode (APD). Additionally or alternatively, sensor(s) 1730 may include additional elements to facilitate taking measurements. For example, sensor(s) 1730 may include an amplifier (e.g., for an APD, etc.), a digital input/output unit, a digital acquisition unit (DAQ) and/or the like. In any embodiments, sensor(s) 1730 may detect a phase lag of light injected via optical source 1720 based on the photons path through tissue. In some embodiments, sensor(s) 1730 collect measurements from a single location on a patient's head. Additionally or alternatively, sensor(s) 1730 may collect measurements from a number of locations on a patient's head.

Optical guide 1740 typically guides light from optical source 1720. For example, optical guide 1740 may split light from optical source 1720 and direct the light to a number of separate locations on a patient's head. In some embodiments, optical guide 1740 includes an optical switch (e.g., a 1×9 switch, etc.). In any embodiments, optical guide 1740 may be or include a waveguide. For example, optical guide 1740 may include a dielectric waveguide, a two-dimensional waveguide, a light pipe, and/or an optical fiber. In any embodiments, optical guide 1740 may split light from optical source 1720 (e.g., from a single transmission point into a number of transmission points).

Power source 1750 typically supplies power for detection device 1700. In some embodiments, power source 1750 is a mobile power source (e.g., a battery, etc.). Additionally or alternatively, power source 1750 may be a stationary and/or fixed power source (e.g., 120 Volt ("V") AC wall charger, etc.). In any embodiments, power source 1750 may receive and store electrical power from a power source for future use (e.g., in remote locations where electricity is not readily available, during a power outage, etc.). Power source 1750 may be or include a solar panel, a power supply (e.g., a 120 Volt ("V") AC wall charger, a 220V AC wall charger, a 240V AC wall charger, etc.), a 12V car adapter, a battery, and/or an external energy storage source (e.g., an energy tank, a battery, etc.).

Display 1760 typically displays information to a user of detection device 1700. In any embodiments, display 1760 may facilitate receiving information from and/or providing information to users of detection device 1700. For example, display 1760 may include a touch-screen display. In any embodiments, display 1760 may present visual information to a user. Display 1760 may be or include an electroluminescent ("ELD") display, a liquid crystal display ("LCD"), a light-emitting diode ("LED") display, an organic light-emitting diode ("OLED") display, a plasma ("PDP") display, a quantum dot ("QLED") display, an E-paper display, and/or any other display technology. In any embodiments, display 1760 may display the location of a detected hemorrhage. For example, display 1760 may display a user-interface ("UI") element corresponding to "no hemorrhage detected" when positioned over tissue not containing a hemorrhage and may display a UI element corresponding to "hemorrhage detected" when positioned over tissue containing a hemorrhage and/or hematoma, etc. In any embodiments, detection device 1700 may have an imaging resolution of about 1 cm or less.

Turning now to FIG. 17(B), an example embodiment of a deployment of detection device 1700 is shown. As shown in FIG. 17(B), detection device 1700 may be configured to communicate and/or interface with a computing device (e.g., a laptop, tablet, PC, etc.) to provide the computing device with measurements, identification, and/or localization information. For example, detection device 1700 may be integrated and/or combined with other diagnostic systems (e.g., computed tomography (CT) systems, functional magnetic resonance imaging (FMRI) systems, etc.) to identify and locate EDH SDH. In some embodiments, components of detection device 1700 may be integrated into a head cap (e.g., to facilitate accurate positioning of optical source 1720, sensor(s) 1730, and/or optical guide 1740, etc.).

Figure 18:
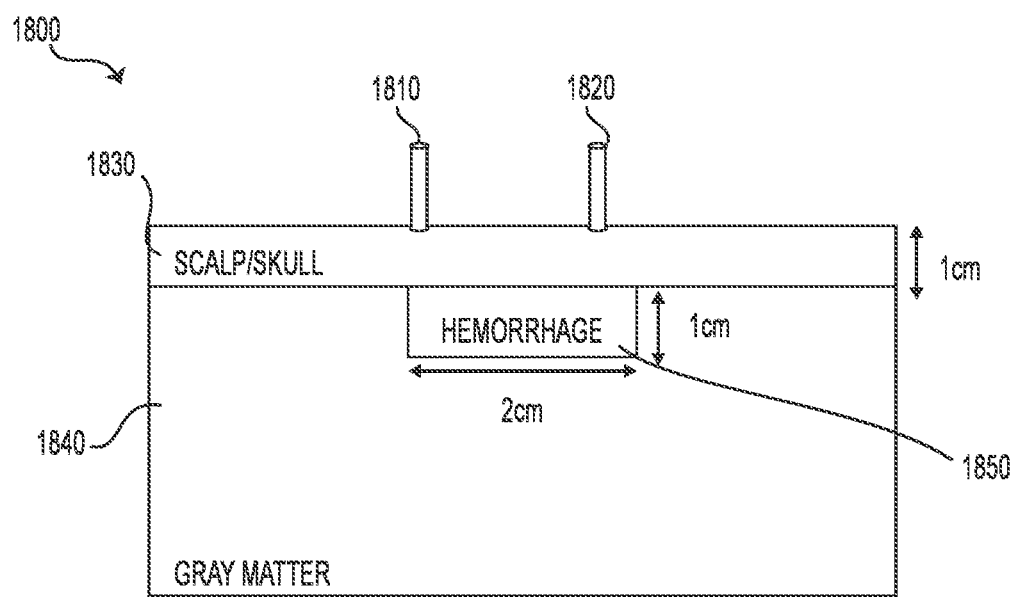
FIG. 18 is a schematic depiction of a simulated hemorrhage that may be detected using frequency-domain diffuse optical tomography (FD-DOT), according to at least one exemplary embodiment.

Turning now to FIG. 18, a schematic of a simulated hemorrhage of a patient's head 1800 identified using frequency-domain diffuse optical tomography (FD-DOT) is shown, according to an exemplary embodiment. In any embodiments, identification of a hemorrhage as shown in FIG. 18, which was constructed using optical phantoms, may be accomplished using detection device 1700. Head 1800 includes first portion 1830 and second portion 1840. First portion 1830 is or includes scalp/skull tissue. Second portion 1840 is or includes brain tissue. For example, second portion 1840 may include gray matter tissue. Second portion 1840 may include hemorrhage 1850. Hemorrhage 1850 may be or include an intracranial hemorrhage such as an EDH or SDH. Hemorrhage 1850 may include a buildup of blood within the skull of the patient. Hemorrhage 1850 may cause intracranial pressure.

In any embodiments, FD-DOT may be used to detect hemorrhage 1850. For example, a user may operate detection device 1700 to detect hemorrhage 1850. FIG. 18 shows transmitter 1810 and receiver 1820. In any embodiments, multiple transmitters and receivers may be provided. Transmitter 1810 may correspond to an output of optical source 1720 and/or optical guide 1740 of detection device 1700. Receiver 1820 may correspond to sensor(s) 1730 of detection device 1700. In any embodiments, transmitter 1810 and receiver 1820 may be spatially related. For example, transmitter 1810 may be horizontally offset from receiver 1820 by a fixed or dynamic distance. In use, transmitter 1810 typically transmits light into head 1800. For example, transmitter 1810 may transmit light into first portion 1830 and the light may diffuse through first portion 1830, second portion 1840, and/or hemorrhage 1850.

In some embodiments, characteristics of the diffused light may be measured by receiver 1820. For example, receiver 1820 may measure an amplitude and/or phase of the diffused light. In any embodiments, detection device 1700 may identify hemorrhage 1850 based on the different optical properties of hemorrhage 1850, first portion 1830, and/or second portion 1840.

Referring now to FIGS. 19-22, results of tissue measurements using FD-DOT to identify a hemorrhage are shown, according to various exemplary embodiments. FIGS. 19-22 illustrate operational measurements of various embodiments of detection device 1700. For example, detection device 1700 may measure optical characteristics of tissue and generate one or more models to facilitate identification and localization of intracranial hemorrhages.

Figure 19:
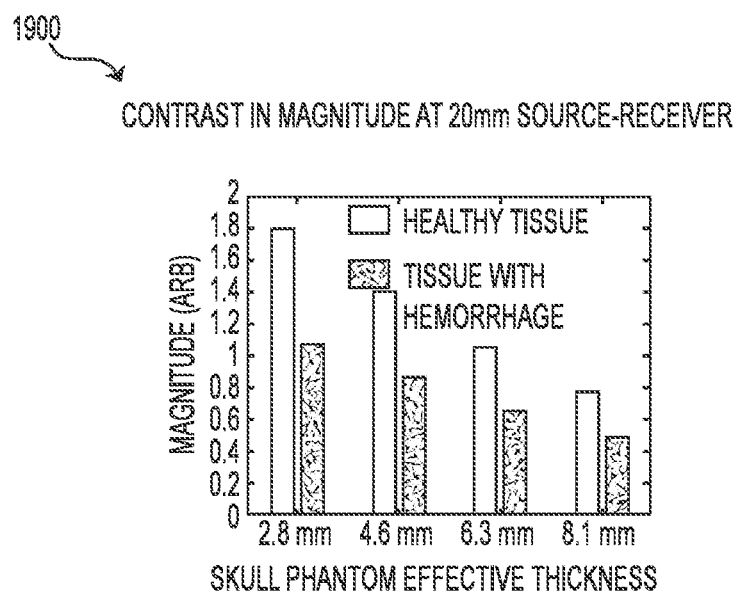
FIG. 19 illustrates an amplitude response of a simulated hemorrhage measured using FD-DOT, according to at least one exemplary embodiment.

Referring specifically to FIG. 19, a graph 1900 is shown illustrating detected light amplitude measurements as a function of skull thickness using FD-DOT to assess sensitivity. In any embodiments, detection device 1700 may collect the data for graph 1900. In this example, graph 1900 includes an x-axis depicting a skull thickness and a y-axis depicting a magnitude of measured light diffused into tissue. In this example, graph 1900 illustrates amplitude measurements based on light generated by optical source 1720 and diffused by different types of tissue. For example, graph 1900 illustrates an amplitude of diffused light from healthy tissue (e.g., tissue not containing a hemorrhage) and non-healthy tissue (e.g., tissue containing a hemorrhage). Graph 1900 illustrates a difference between the amplitude of measured light from healthy tissue vs. non-healthy tissue and indicates that the detection device 1700 is sensitive to hemorrhage without utilizing the difference in amplitude of measured light between the healthy tissue and non-healthy tissue to detect a hemorrhage. Typically, tissue containing a hemorrhage has a lower magnitude (e.g., intensity, etc.) of measured diffused light than tissue not containing a hemorrhage.

Figure 20:
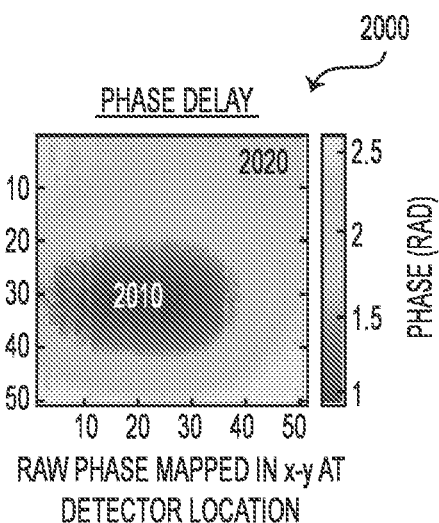
FIG. 20 illustrates a phase response of simulated tissue measured using FD-DOT, according to at least one exemplary embodiment.

Referring now specifically to FIG. 20, a graph 2000 is shown illustrating phase measurements of simulated tissue taken using FD-DOT, where the tissue is an optical phantom designed to mimic subdural hemorrhage. In any embodiments, detection device 1700 may collect the data for graph 2000. In this example, graph 2000 includes an x-axis depicting an x-axis position (e.g., of the position of the measurement on the patient's head), a y-axis depicting a y-axis position (e.g., of the position of the measurement on the patient's head), and a phase of the measured signal. In this example, graph 2000 illustrates phase measurements based on light generated by optical source 1720 and diffused by different types of tissue. For example, portion 2010 of graph 2000 corresponds to phase measurements corresponding to a hemorrhage in tissue and portion 2020 of graph 2000 corresponds to phase measurements corresponding to normal, non-hemorrhaging tissue. In any embodiments, detection device 1700 may utilize the difference in phase of measured light between the healthy tissue and non-healthy tissue to detect a hemorrhage.

In any embodiments, an absorption model may be constructed based on light measurements taken of simulated tissue using FD-DOT. In any embodiments, the detection of a simulated hemorrhage that is displaced (e.g., laterally, etc.) away from the immediate measurement location of detection device 1700 may be modeled. In any embodiments, detection device 1700 may collect data representing absorption values of measured tissue. The data may include Cartesian data relating to an x-axis position of the measurement on the patient's head, a y-axis position of the measurement on the patient's head, and/or a z-axis position corresponding to a depth of the measurement (e.g., a depth under the surface of the patient's head that the light penetrates, etc.), and optical absorption values (AU) associated with the tissue under analysis.

Figure 22A:
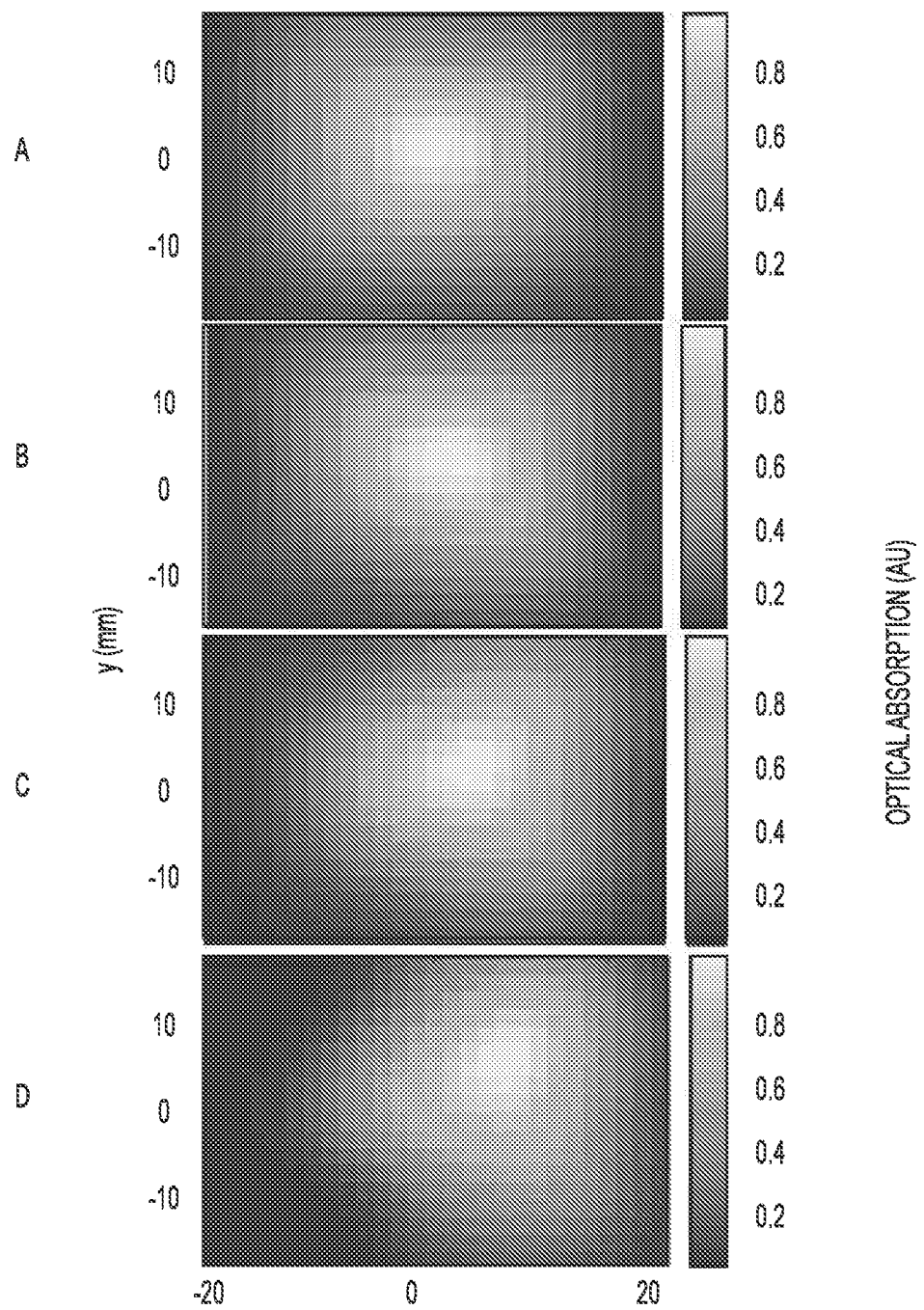
FIG. 22(A) illustrates tomographic reconstruction data obtained in accordance with at least one embodiment.
Figure 22B:
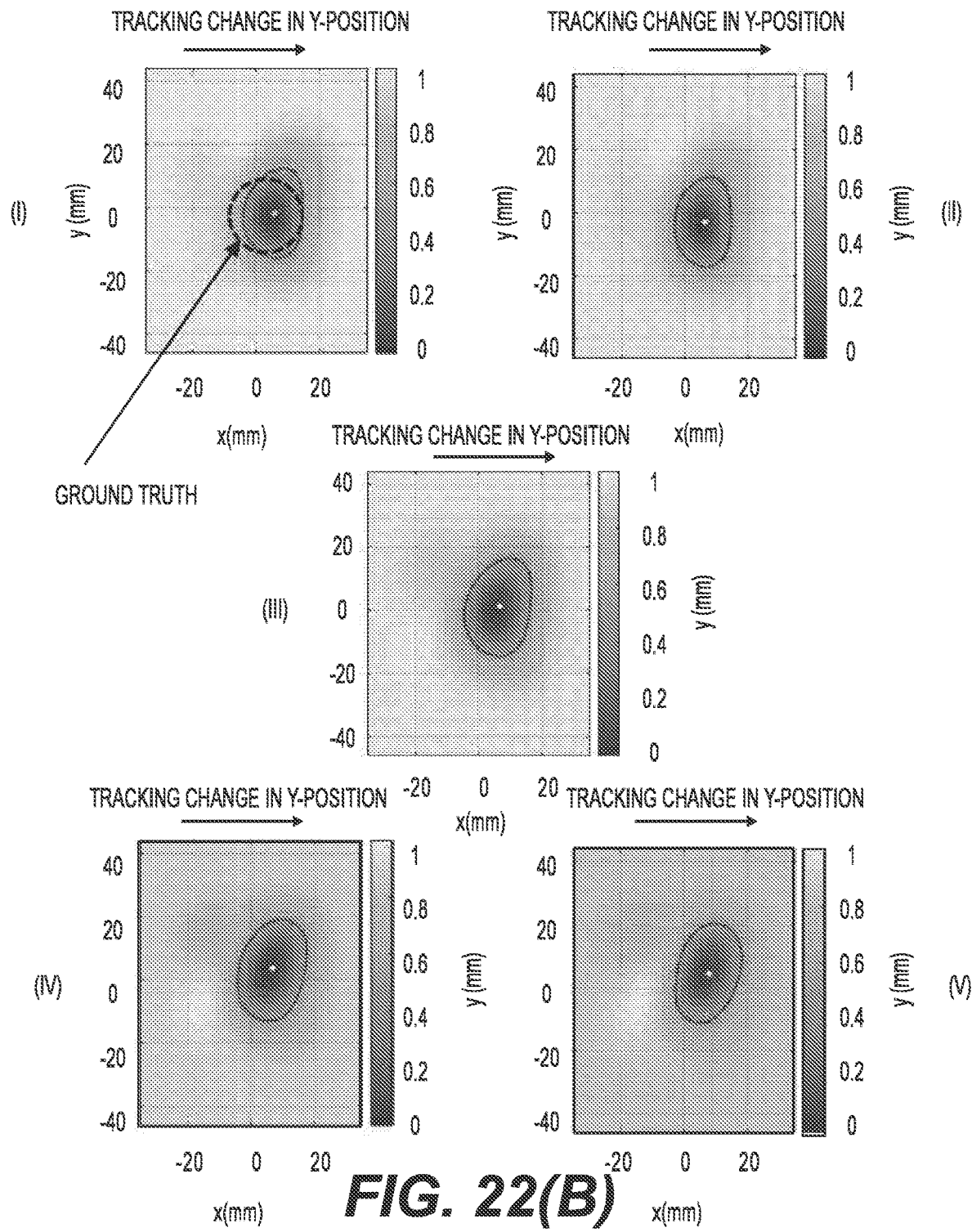
FIG. 22(B) illustrates tomographic reconstruction data obtained in accordance with at least one embodiment.

FIG. 23(A) depicts a three-dimensional plot of an absorption model based on light measurements taken of tissue using FD-DOT, and FIG. 23(B) and FIG. 23(C) depict two-dimensional plots corresponding to top and front views, respectively, of the reconstruction shown in FIG. 23(A). FIG. 22(A) depicts tomographic reconstruction of a hemorrhage to track the lateral position (shown in frames A-D), where the hemorrhage location shifted about 5 mm in a lateral direction. FIG. 22(B) depicts changes in the y-position of the hemorrhage (shown in the progression of frames I-V), where the circled area of the left-most panel indicates the hemorrhage location and size estimated using detection device 1700. The center of the circle, corresponding to the estimated hemorrhage, was slightly offset (e.g., about 3-5 mm) from the actual hemorrhage location. In any embodiment, a multichannel detection device 1700 may generate and/or collect the data as shown in FIGS. 22(A)-22(B) and/or FIGS. 23(A)-23(C). FIGS. 22(A)-22(B) depict a simulated hemorrhage that is displayed (e.g., laterally, etc.) from the immediate measurement location (e.g., a center of, etc.) of detection device 1700. The expected spatial resolution for an FD-DOT system is 1 cm, with the 3-5 mm difference noted above reflecting accurate estimation by detection device 1700 of the size and/or location of detected hemorrhages.

Graph 2100 illustrates optical absorption values based on light generated by optical source 1720 and diffused by different types of tissue. In this example, portion 2110 corresponds to optical absorption values corresponding to tissue having a hemorrhage, and portion 2120 corresponds to optical absorption values corresponding to tissue not having a hemorrhage. In any embodiments, detection device 1700 may determine optical absorption values based on the measured amplitude and phase of light diffused by tissue.

Figure 21:
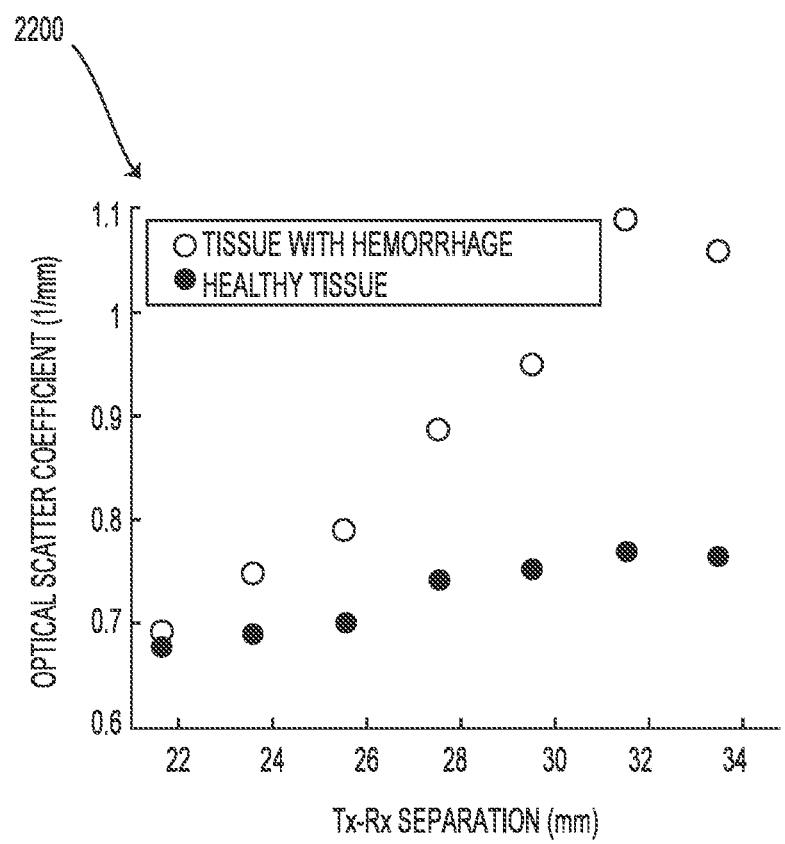
FIG. 21 illustrates optical scatter coefficients determined by measuring tissue using FD-DOT, according to at least one exemplary embodiment.

Referring now specifically to FIG. 21, a graph 2200 is shown illustrating optical scatter coefficients based on light measurements of tissue taken using FD-DOT. In any embodiments, detection device 1700 may collect the data for graph 2200. In this example, graph 2200 represents optical scatter coefficients associated with tissue. In this example, graph 2200 includes an x-axis depicting a separation distance between a transmitter and a receiver. For example, a distance between transmitter 1810 and receiver 1820 as shown in FIG. 18. In any embodiments, the transmitter may be optical source 1720 and the receiver may be one of sensor(s) 1730. In this example, graph 2200 includes a y-axis depicting a magnitude of the optical scatter coefficient associated with the tissue. In this example, graph 2200 illustrates optical scatter coefficients based on measurements of tissue diffused light generated by optical source 1720.

Graph 2200 illustrates a difference in the optical scatter coefficient associated with healthy tissue vs. the optical scatter coefficient associated with tissue having a hemorrhage. For example, the optical scatter coefficient associated with healthy tissue may be below the optical scatter coefficient associated with tissue having a hemorrhage for a Tx-Rx separation of about 32 mm. In any embodiments, detection device 1700 may utilize the differential optical scatter coefficient of tissue to identify and/or locate hemorrhages. For example, detection device 1700 may identify a hemorrhage based on an absolute value of the optical scatter coefficient associated with tissue and/or based on a relative optical scatter coefficient associated with tissue (e.g., by comparing the optical scatter coefficient associated with potentially hemorrhaging tissue to that of nearby healthy tissue, etc.).

Hemorrhage Extraction

According to at least one embodiment, intracranial access device 1 is configured to create, via a drill, a circular burr hole through the cranium, while optionally applying electrocautery to stop local bleeding. The burr hole can serve as an access hole, as discussed below in more detail.

Once the burr hole has been created, an operator can extract the hemorrhage, such as by inserting a sterile, large bore needle through membrane R of the device 1 into the bore hole. Typically, inserting the needle about 1 cm past the housing will reach the surface of the skin, while inserting the needle about 1.5 cm to about 2 cm further will reach a hemorrhage. The insertion of the needle to reach the hemorrhage may take about 1 minute or less to accomplish. In some embodiments, the needle may remain in place to relieve pressure on the brain, such as by draining pressure in the case of EDH or high pressure SDH. In some embodiments, such as when the hemorrhage is a low pressure SDH, the operator may apply suction (negative pressure) to extract the hemorrhage, such as by using a syringe. For a high pressure SDH, blood may spontaneously enter a needle, whereas in a low pressure SDH, an operator may need to apply suction, such as via a syringe.

In any embodiments, the needle may be sequentially positioned at a plurality of angles, and/or the patient may be repositioned to promote effective drainage of multi-compartmented hemorrhages or partially closed hemorrhages. In some embodiments, the device 1 is used to partially remove some of the blood, such as to remove critical, life-threatening elevated intracranial pressure (and not necessarily to completely treat a brain injury itself).

Additionally or alternatively, in some embodiments, a side cutting device may be employed, which is akin to a miniaturized version of the NICO Myriad® morcellator made by NICO Corporation of Indianapolis, IN The side cutting device is a morcellator that may be used to remove clotted or partially clotted blood having a gel-like consistency. The morcellator may be inserted into the burr hole to cut and then aspirate the clotted blood. More particularly, the side cutting blade alternates up and down while applying suction through the cranial burr hole. A small amount of material is sucked into the burr hole, cut, then aspirated through a hollow bore tube into the collection system. This process may be repeated many times in quick succession until the bulk of the material has been cut and removed.

In some embodiments, the time from hemorrhage identification to relief of pressure may be under 15 minutes. In some embodiments, multiple hemorrhages may be removed during a single treatment session if intracranial bleeding continues.

Access Hole

As described above, the device described herein may be employed to create an access hole in the cranium that is protected from the environment by the device, including membrane R. The access hole permits intracranial diagnosis and treatment. The access hole may be dimensioned so as to accommodate one or more items to access the cranium, including, but not limited to, a pressure probe or transducer, an aspiration needle, a tissue removal device, a syringe, or a medicament.

In some embodiments, the access hole allows direct injection of medicine into the brain, without further trauma and with a relatively low risk of infection, due to the protection provided by the device. Thus, in some embodiments, the device may be used to administer one or more medications directly into the brain through the access hole, such as using a sterile needle inserted through membrane R, so as to reduce the risk of intracranial infections. Medications that may be advantageously administered directly to the brain include, but are not limited to, antibiotics, antiepileptics, pro-coagulants, hemostatics, and other neuroprotective medications. Additionally or alternatively, antibiotics may be delivered intravenously to penetrate throughout the brain and the circulation system, reducing infection and the risk of infection at other sites.

Further, the access hole may provide for placement of additional intracranial monitoring, without further trauma, and with a relatively low risk of infection. For example, monitoring devices to measure intracranial properties may be inserted, including one or more of an intracranial pressure monitor, a brain oxygen monitor, a brain blood flow monitor, and a brain temperature monitor. Further, one or more probes may be inserted for microdialysis, including inline probes for glucose, lactate and pyruvate monitoring.

Figure 11:
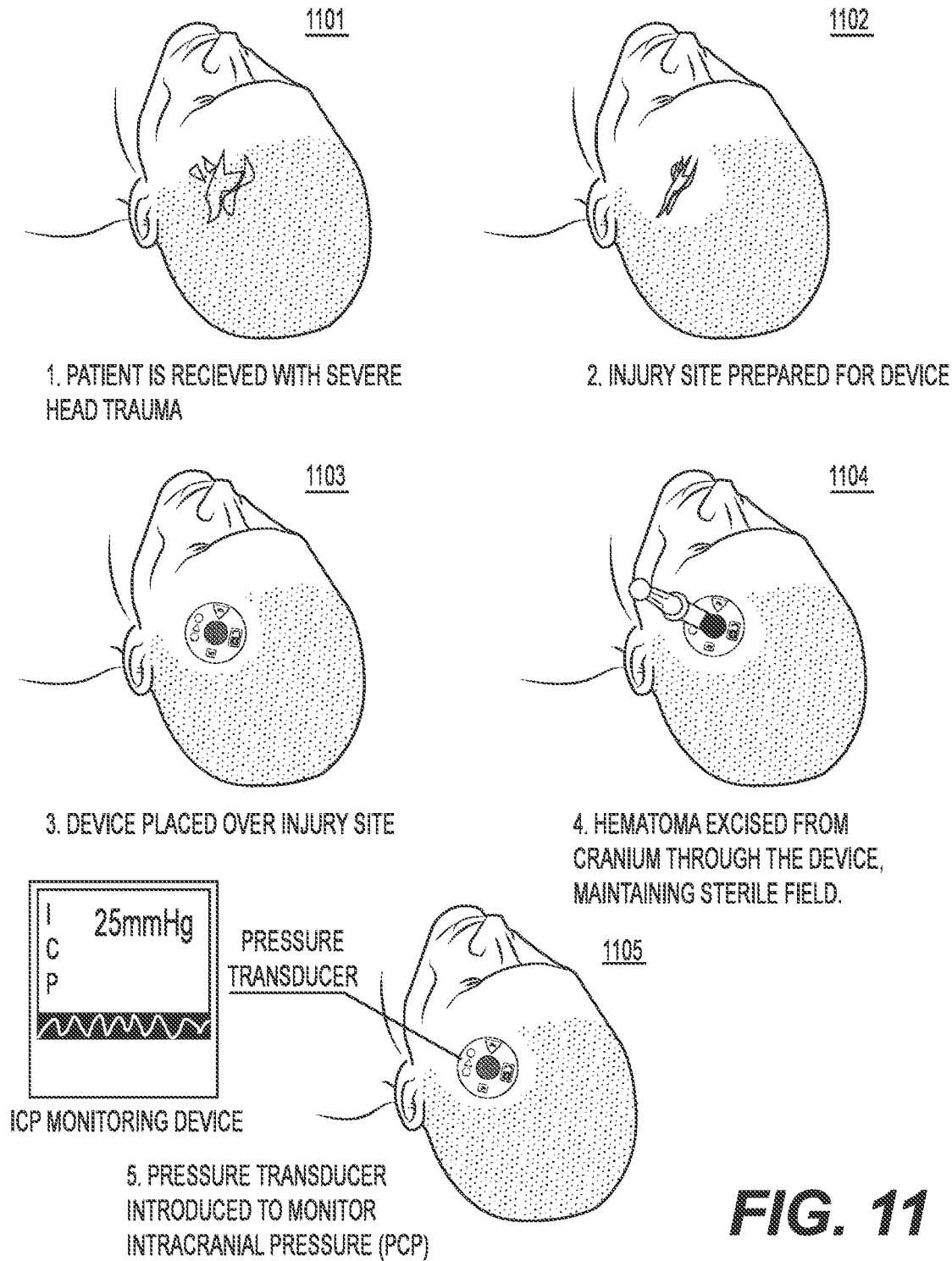
FIG. 11 depicts a process according to at least one embodiment described herein.
Figure 12A:
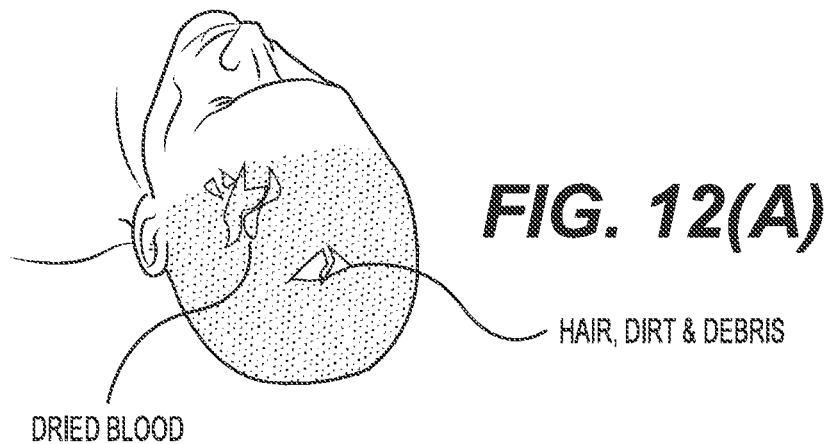
FIG. 12(A) is a top view of a patient to be treated in accordance with at least one embodiment described herein.
Figure 12B:
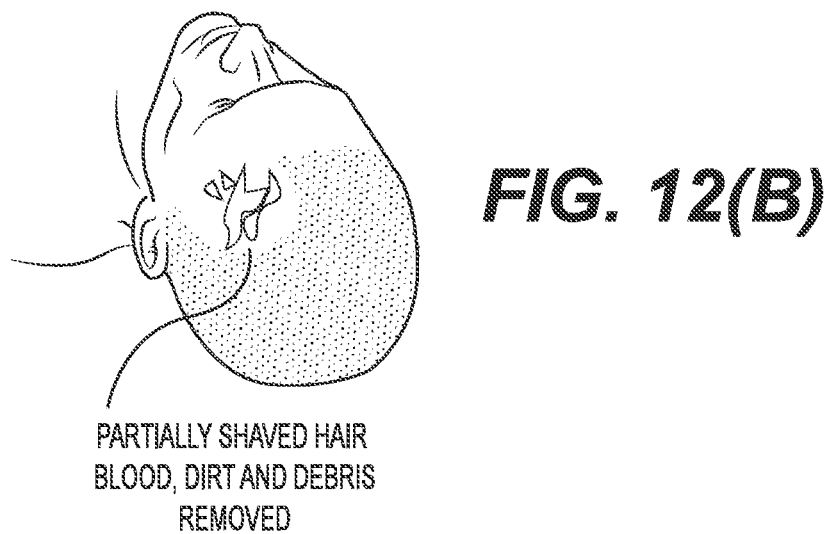
FIG. 12(B) is a top view of a patient prepared for treatment with a device as described herein.

In some embodiments, a miniaturized intracranial pressure monitor M, as shown in FIG. 11, may be provided. The monitor is configured to communicate with an access port at the cranium so as to take intracranial pressure readings from one or more locations within the cranium. The monitor may comprise one or more pressure sensors such as pressure transducers configured to communicate with a controller (e.g., a microcontroller having a memory and a processor, and a communication interface configured to receive signals from the one or more pressure sensors). In some embodiments, the monitor comprises a display configured to display, on a display screen, an output of one or more pressure readings from the one or more locations within the cranium.

In some embodiments, access hole 1590 (as shown in FIG. 15(B)) is similar to the access hole described above. In any embodiments, access hole 1590 may be an opening in a surface of lid 1516 that facilitates access to treatment area (e.g., passage of instruments from an external area into a treatment area at least partially sealed by access device 1500, etc.). In any embodiments, access hole 1590 may be axially aligned with tube 1576. In some embodiments, access hole 1590 is covered by membrane 1592 (as shown in FIG. 15(I)). Membrane 1592 may at least partially seal access hole 1590. In any embodiments, membrane 1592 may be a silicone membrane. Membrane 1592 may be punctured by instruments during treatment of a hemorrhage. For example, a user may insert a needle through membrane 1592 to withdraw fluid from a hemorrhage via a burr hole created by access device 1500.

Power Supply

The components described herein may receive power from at least one of an internal power supply or an external power supply. An internal power supply may be a power component that is integrated with drill assembly 7, such as a battery provided in the same internal housing as the drill or components coupled to the drill. For example, as shown in FIG. 8(A), the battery may be a battery pack BP. In some embodiments, wires from the battery pack BP may be used to carry out electro cauterization, as discussed above.

In some embodiments, an external power source may be provided in lieu of or in addition to an internal power source. An external power source may be a battery pack with a rechargeable power supply, such as one or more foldable solar panels and/or a hand crank. In some embodiments, the IR sensors 11, drill assembly 7, side cutting device and others may be powered from an external universal lithium ion power source, to save weight and space in a medic's kit. The power pack may be thermally insulated to operate at extreme temperatures. Further, the power pack and the components described above may include universal rugged connectors and ports so as to mitigate contamination or degradation in field environments.

Method of Using Intracranial Access Device

An intracranial access device as described herein can be used to create burr holes in a cranium and relieve intracranial pressure, such as may arise from subdural or epidural hemorrhage, and to monitor intracranial pressure, such as in the event of diffuse swelling.

According to some embodiments, a method for relieving intracranial pressure of a patient in need thereof is provided. The method incudes positioning an intracranial access device on a surface of the patient's head and activating an intracranial access device as described herein to create an intracranial burr hole. Intracranial fluid may be withdrawn through the intracranial burr hole to relieve intracranial pressure.

According to some embodiments, a method for monitoring intracranial pressure of a patient in need thereof is provided. The method incudes positioning an intracranial access device as described herein on a surface of the patient's head, activating the intracranial access device to create an intracranial burr hole, and inserting an intracranial pressure monitor through the intracranial burr hole.

The use of an intracranial access device as described herein allows for a relatively clean environment to be maintained at an injury site, including for periods of prolonged care in a field setting, e.g., for up to 72 hours or longer.

FIG. 11 depicts a process 1100 according to at least one embodiment. At step 1101, a patient is received with a severe head trauma. Next, at step 1102, the injury site is prepared. At step 1103, the device is positioned, and a sterile area may be established. At step 1104, the hemorrhage is extracted while maintaining the sterile area. At step 1105, the patient is monitored, e.g., with one or more sensors inserted into the burr hole.

More particularly, step 1101 may include, in addition to receiving a patient with head trauma, evaluating the severity of the trauma to determine whether EDH or SDH is present. For example, in less than about 2 minutes, an operator may determine whether one or more of the following criteria are satisfied: (a) the patient is in a coma or has a markedly reduced level of consciousness, with a Glasgow coma score of less than or equal to 8; (b), there is evidence of head trauma; (c) one or both pupils are non-reactive, or (d) there is no other apparent explanation for a reduced level of consciousness.

At step 1102, the injury site may be prepared in the following manner. The patient is positioned with his or her head at a 30° angle, and with the neck in a neutral position. The operator shaves and cleans the patient's head or a portion thereof, in less than two minutes.

Figure 13A:
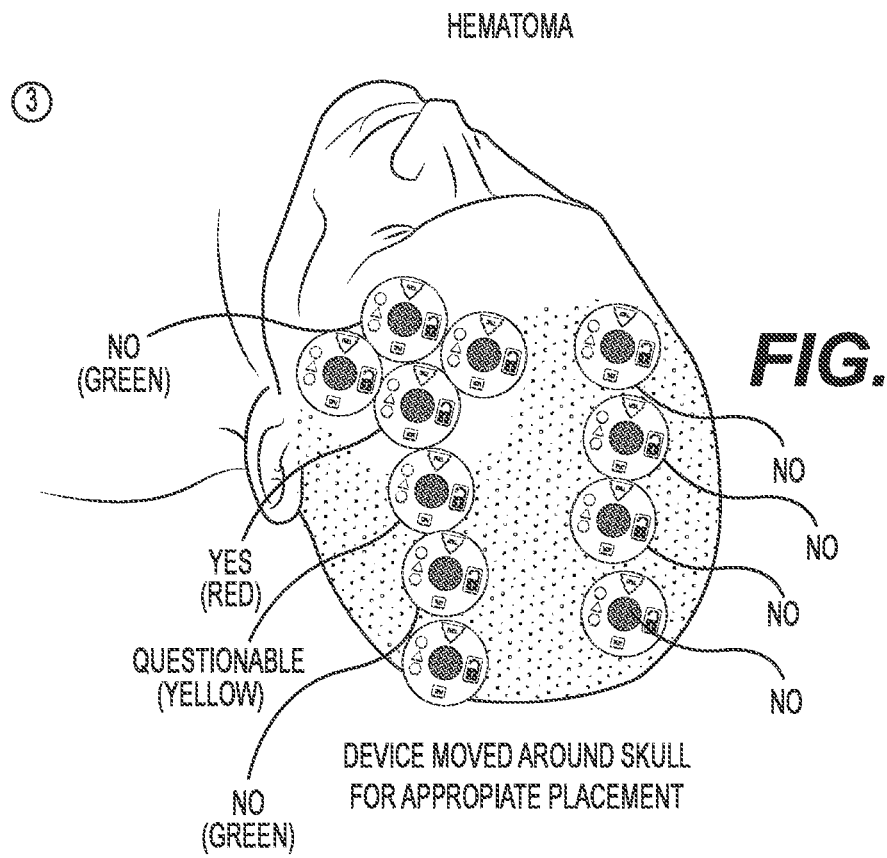
FIG. 13(A) illustrates the detection of a hematoma site and placement of a device as described herein, according to at least one embodiment.
Figure 13B:
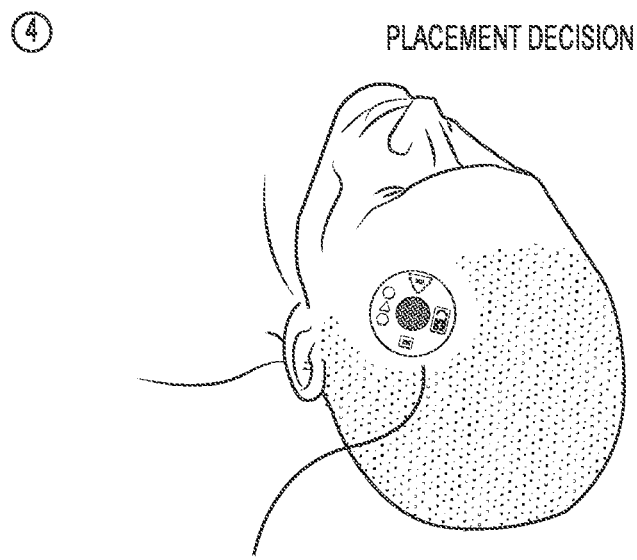
FIG. 13(B) illustrates the detection of a hematoma site and placement of a device as described herein, according to at least one embodiment.
Figure 14A:
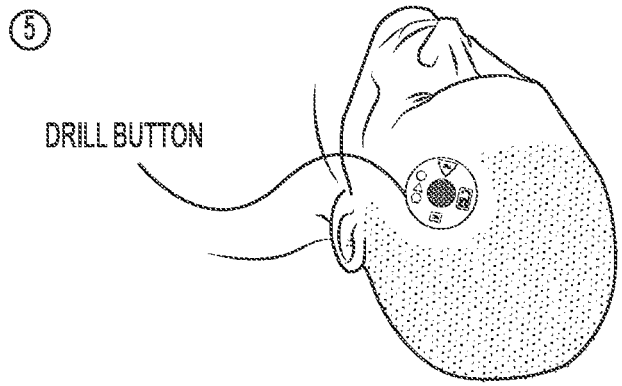
FIG. 14(A) illustrates deployment of a device as described herein in accordance with at least one embodiment.
Figure 14B:
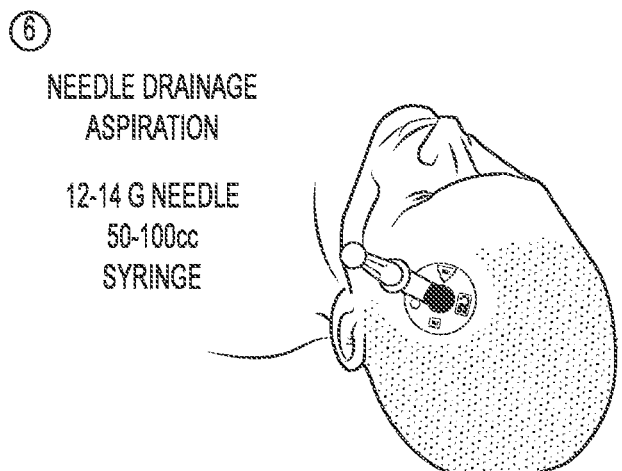
FIG. 14(B) illustrates aspiration/draining of fluid using a device as described herein in accordance with at least one embodiment.
Figure 14C:
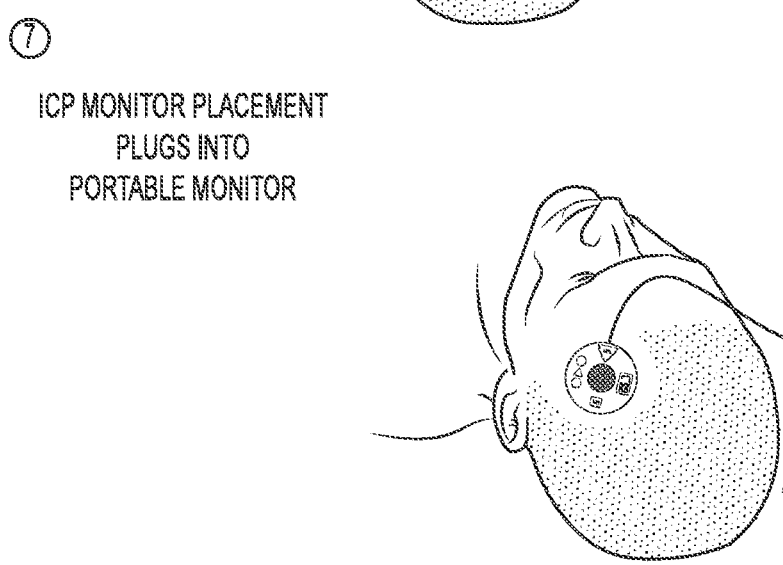
FIG. 14(C) illustrates monitoring of intracranial pressure using a device as described herein in accordance with at least one embodiment.

At step 1103, the intracranial access device 1 is positioned at a site identified as a hemorrhage location. The operator may position the device 1 at one of a plurality of standard locations (e.g., twelve standard locations, six being on a first half of the cranium and six being on a second half). Some of the twelve locations may be locations shown in FIG. 13(A), for example.

In some embodiments, the process further includes employing sensors on the device to identify a hemorrhage location. To localize and visualize hemorrhage sites, the intracranial access device 1 may be used to employ NIR spectroscopy, as discussed above, to detect whether fluid (e.g., blood) is present in the epidural or subdural layers, and to output a result of that detection to the operator. In some embodiments, the detection step is optional.

According to some embodiments, hemorrhage detection results may be outputted audio visually. In some embodiments, the detection result may be outputted via the LEDs L1-L3 on the device 1 and/or via displays of symbols on the device or on a display connected to the device 1. For example, L1 may indicate a first detection result that no blood is detected, corresponding to a symbol of '0'; L2 may indicate a second detection result that there is an uncertain or poor reading, with a symbol of "?", and L3 may indicate a third detection result that blood is present, corresponding to a symbol of "+." The brightness of the light may indicate the relative amount of blood present. According to some embodiments, the indicators L1-L3 may be vibratory or use another form of haptic feedback. The operator may position the device 1 sequentially at two or more or all of a plurality of standard locations (e.g., at two or more or all of the twelve standard locations), and obtain detection results for each position. Alternatively, the operator may position the device 1 sequentially at a plurality of locations until a positive result (detection of a hemorrhage) is obtained. If localization results are uncertain, additional detection may be performed.

In some embodiments, the operator marks the result (or corresponding symbol) on the patient's shaved head, and then identifies a site to position the device 1, e.g., a location central among the positive position result locations where blood was detected.

Alternatively, the location may be selected not based on hemorrhage location, but on the integrity of the overlying bone. For example, where a skull fracture is visible, it may be difficult to obtain a good seal directly over such a location, and so the risk of infection is heightened. Accordingly, a site away from a skull fracture, toward the edge of the hemorrhage, may be selected.

At step 1104, once the site is selected, the device is positioned and locked into place (such as by deploying the fasteners), and then drilling is carried out using the drill 9 as described above in regard to FIGS. 1(A)-1(B). Then, intracranial pressure may be relieved, such as by inserting a sterile needle and/or using a syringe. At step 1105, the patient is monitored, e.g., with one or more sensors inserted into the burr hole, optionally via the open drill bit 9.

In at least one embodiment, at step 1104, the device 1 is placed over a chosen location, and the operator applies firm pressure. The device 1 then deploys the plurality of fasteners 3 to fasten the device 1 to the cranium. (As noted above, each fastener 3 may be equipped with a plurality of hooks 4, such as barbs, which extend from lateral sides of the fasteners 3, which further assist with securing the fasteners 3 in place.) As shown in FIG. 7, after the fasteners 3 are inserted into the cranium (e.g., after the lock button B2 is pressed), they may be pulled back slightly so as to ensure compression of the gasket 12 and maintain a tight seal between the skull and the device 1.

In at least one embodiment, the intracranial device 1 performs a self-diagnostic routine when its power supply is first turned to an ON state, or when a test button (such as button B3) is actuated. The self-diagnostic routine may, for example, take about 1 minute or less to perform. Further, after turning the power supply to the ON state, an operator may check whether the device 1 has sufficient battery power to perform detection, burr hole creation, and cautery, for example. In particular, a display screen of a monitor in communication with the device 1 may display a charge state of the battery in terms of bars and/or in terms of a percent, graphically and/or numerically. When the power is insufficient, the operator may plug in the intracranial device 1 (e.g., at 110V, 220V, USB power, etc.) replace the battery, which may be a lithium ion battery. When the power is sufficient, the device 1 may be set in a 'ready' or 'standby' mode.

Figure 16:
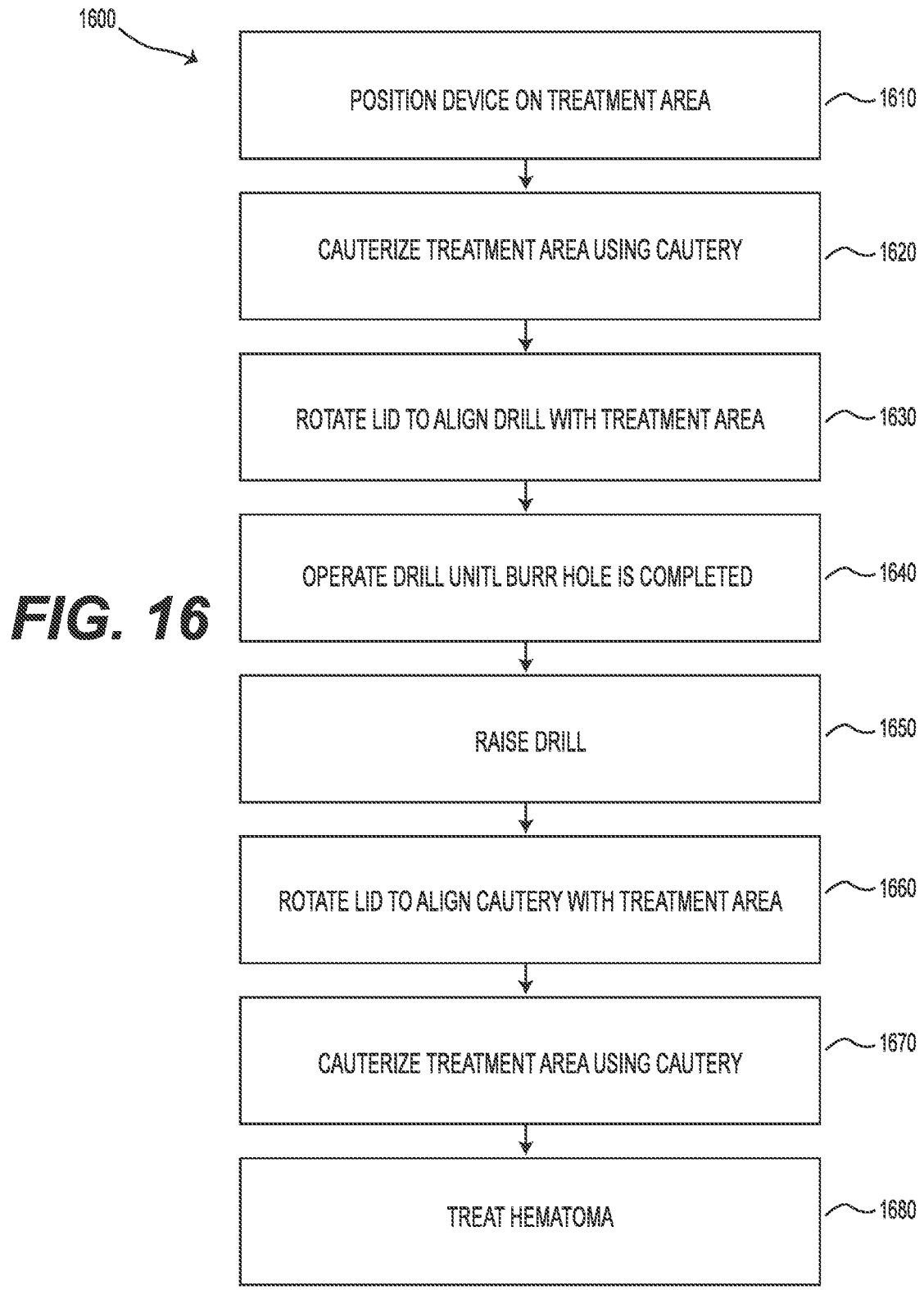
FIG. 16 illustrates a method of relieving intracranial pressure using an intracranial access device, according to an exemplary embodiment.

Referring now specifically to FIG. 16, method 1600 for relieving intracranial pressure using an intracranial access device is shown, according to an exemplary embodiment. In any embodiments, method 1600 may utilize access device 1 or access device 1500 and/or detection device 1700 as described above. For example, a user may operate detection device 1700 to facilitate diagnosing a source and/or location of intracranial pressure (e.g., localized hematoma, etc.) and may operate access device 1500 to facilitate treatment and/or monitoring of the intracranial pressure.

In some embodiments, method 1600 includes diagnosing and/or localization of a source of intracranial pressure. For example, a user may operate detection device 1700 by scanning detection device 1700 over a surface of a patient's head to identify a hematoma. In some embodiments, method 1600 as described herein is effected after a position of intracranial pressure has been identified (e.g., by using detection device 1700 or otherwise, etc.).

At step 1610, a user may position access device 1500 on a treatment area of the patient. In any embodiments, the treatment area may include a portion of the patient's head. In some embodiments, the treatment area is previously identified using detection device 1700. For example, a user may operate detection device 1700 to identify a location of a subdural hemorrhage on a patient's head and may mark the location as the treatment area. In any embodiments, step

1610 may include fastening access device 1500 to the patient's head. For example, a user may fasten access device 1500 to the patient's head using adhesive and sealing element 1520 and/or bone screws. In some embodiments, step 1600 includes preparing a surface of the patient's head prior to positioning of access device 1500. For example, a user may shave the treatment area to remove hair and/or may sterilize the treatment area prior to positioning access device 1500.

At step 1620, the user may cauterize the treatment area using cauterizer 1570. In any embodiments, step 1620 may include positioning cauterizer 1570 over the treatment area by rotating lid 1516 such that a cautery element is positioned directly over the intended burr hole location. In any embodiments, step 1620 may include operating cauterizer 1570. For example, the user may power and depress plunger 1574 a number of times (e.g., 2 or 3 times, etc.). In some embodiments, step 1620 is optional.

At step 1630, the user may rotate lid 1516 to align drill 1540 with the treatment area. In any embodiments, step 1630 may include positioning drill 1540 directly above the cauterized area from step 1620. In some embodiments, step 1630 includes securing a rotational position of lid 1516. For example, the user may rotate lid 1516 to align drill 1540 above the treatment area and then may lock lid 1516 to prevent further rotation and/or misalignment.

At step 1640, the user may operate drill 1540 to create a burr hole. Operation of drill 1540 may include rotating handle 1542. For example, the user may rotate handle 1542 until drill 1540 has fully penetrated the skull. In any embodiments, a user may detect that drill 1540 has fully penetrated the skull by identifying a sudden drop in torque required to rotate handle 1542 as drill 1540 penetrates the skull. In any embodiments, step 1640 may include manual operation of drill 1540 (e.g., by manually rotating handle 1542). Additionally or alternatively, step 1640 may include assisted and/or automated operation of drill 1540 for example through assisted and/or automated rotation of handle 1542 (e.g., by a motor, etc.). In some embodiments, operation of drill 1540 includes clockwise rotation of handle 1542. Additionally or alternatively, operation of drill 1540 may include counterclockwise rotation of handle 1542 (e.g., to clear debris during formation of the burr hole, etc.).

At step 1650, the user may raise drill 1540. For example, the user may remove drill 1540 from the newly created burr hole to facilitate access to the burr hole. In any embodiments, step 1650 may include counterclockwise rotation of handle 1542. Additionally or alternatively, step 1650 may include clockwise rotation of handle 1542. It should be understood that other means for raising drill 1540 are possible and that step 1650 is not limited to the examples expressly contemplated herein. For example, step 1650 may include decoupling drill 1540 from access device 1500 and removing drill 1540 from the burr hole.

At step 1660, the user may rotate lid 1516 to align cauterizer 1570 with the treatment area. In any embodiments, step 1660 may include locking and/or unlocking lid 1516 to facilitate rotation as discussed above. In any embodiments, step 1660 may include positioning a cautery element directly over the burr hole.

At step 1670, the user may cauterize the treatment area (e.g., the burr hole, etc.) using cauterizer 1570. Similarly to step 1620, step 1670 may include operating cauterizer 1570 by powering and depressing plunger 1574 a number of times (e.g., 2-3 times, etc.). In some embodiments, step 1670 is optional.

At step 1680, the user may treat the patient's hematoma via the burr hole. For example, the user may remove epidural or subdural blood using a needle and/or syringe. Additionally or alternatively, the user may monitor intracranial pressure associated with the patient. It should be understood that many treatment modalities are possible given the physical access facilitated by the newly created burr hole and such treatment modalities (e.g., monitoring, removal of blood, etc.) are not limited to the examples expressly set forth herein.

Example 1: Exemplary Method

An operator uses an intracranial access device as described herein that is 3 cm diameter and 1 cm thick, and places it on the shaved head of an unconscious patient, and then (1) detects the presence of epidural and subdural blood in the intracranial space underlying the site of the device; (2) positions the device accordingly and deploys the fasteners to clamp the device tightly to the aseptic skin and skull; (3) actuates the retractor blades to make a circular incision in the skin and then actuates the drill to make a circular burr hole through the cranium, while applying electrical cautery to stop local bleeding; (4) drains epidural or subdural blood using a needle inserted through the membrane R, while reducing risk of infection in a potentially non-aseptic environment; (5) optionally, directly injects medications into the brain without further trauma and with relatively low risk of infection, and (6) optionally, places additional intracranial monitoring devices without further trauma and with relatively low risk of infection.

Example 2: Exemplary Protocol

Total time from identification to relief of elevated intracranial pressure is under 15 minutes.
- Operator identifies patient who could have an intracranial hemorrhage (under 2 minutes).
- Operator turns on device, which goes through self-diagnostic mode in under 1 minute and confirms sufficient battery power to perform detection, burr hole, and cautery procedure.
  - If insufficient power, operator plugs in device to 110V, 220V, USB power, or replaces Lithium ion (or other) high power batteries.
  - If sufficient power, device goes into 'ready' mode.
- Operator places the patient with head at 30 degree angle and neck in neutral position.
- Operator quickly shaves and cleans head (goal is to remove most of the hair, dirt and dried blood that would interfere with infrared detection) (under 2 minutes).
- Operator sequentially places the device on the head in each of 12 standard locations, 6 on each side, requiring under 3 minutes total.
  - At each location, device signals green "0" for no blood, red "+" for blood, and orange "?" for uncertain or poor reading.
  - Operator marks "0", "+", or "?" at each site on the head with Sharpie-type permanent marker (1-inch marker included, clipped to the device as part of the kit)
  - Operator chooses the optimal location, most likely the central location among the cluster of those marked as "+".
  - Additional locations can be scanned in case the optimal location is not clear. Some operator judgment will be required.

Alternatively, the infrared detection function could be incorporated using a separate hand held device.

Operator places the device over the optimal location, applies firm pressure, and triggers the device. (The optimal location will take into account the location of the hemorrhage and the integrity of the overlying bone. It may be difficult to get a good seal over a skull fracture. A site away from fractured skull and toward the edge of the hemorrhage may be preferred.)

The device extends 6 anchors through the scalp and 2 mm into the outer table of the skull which lock the device into place using deployed barbs.

Operator confirms that the device is solidly locked in place.

Operator triggers the device again.

The device deploys a high-speed alternating blade which cuts through the skin and a telescoping burr that drill through the skull, applying electrocautery to stop local bleeding. (The operator may clamp the superficial temporal artery in the temporalis muscle if it is severed during the approach.)

The device uses infrared sensors and detects resistance to applied force to determine when it has penetrated the skull and reached the hemorrhage.

The device stops automatically when it has reached the hemorrhage or its maximum depth of 2 cm.

The telescoping burr retracts and dilates in an iris-like fashion, leaving an open burr hole with direct access to the intracranial space.

The device alerts and flashes when complete (under 5 minutes).

The device displays the depth required to penetrate the skull and reach the hemorrhage for the operator's use in drainage.

The operator inserts a sterile, large bore needle through the outer device membrane, then a further 1 cm to reach the surface of the skin plus a further 1.5-2 cm typically to reach the hemorrhage (under 1 minute).

The operator can leave the needle open to allow pressure driven drainage of an epidural hemorrhage or high pressure subdural hemorrhage.

The operator can use a syringe to apply suction to a low pressure subdural hemorrhage.

The operator can reposition the needle at several angles and reposition the patient for optimal drainage of multi-compartment or partially clotted hemorrhage. This requires some judgement on the part of the operator.

The main goal is to reduce life-threatening elevated intracranial pressure. The operator does not have to remove all of the blood.

Alternatively, the operator inserts a side cutting device similar to a miniaturized version of the NICO Myriad® to remove partially clotted blood with a gel-like consistency.

Optionally, the operator gives antibiotics to the patient to reduce the risk of intracranial infections.

If intravenous access is available, this route is preferred since antibiotics will penetrate throughout the brain and systemic circulation, also reducing risk infection at other sites.

If intravenous access is not available, antibiotics can be administered directly into the brain through the device membrane using a sterile needle.

Optionally, the operator gives anti-epileptic, pro-coagulant, hemostatic, or other neuroprotective medications directly into the brain through the device membrane.

Optionally, the operator inserts advanced monitoring devices into the brain through the device membrane to guide the extent of hemorrhage evacuation and other interventions, such as to monitor:
  a. Intracranial pressure
  b. Brain oxygen
  c. Brain blood flow
  d. Brain temperature
  e. Microdialysis attached inline to real time glucose, lactate and pyruvate monitors.

Typically, the operator records all invasive actions including date and time using the device in marker/pen written on the scalp.

Typically, the operator records all systemic interventions including date and time in pen written on the chest.

Typically, the device remains locked in place until definitive neurosurgical hospital treatment is available. It is removed in the operating room using a key mechanism. If required, it can be removed in the field using a key mechanism, but it is designed not to come off easily even under rigorous conditions.

Even when used properly, multiple hematoma evacuations may be required because in a large proportion of cases, intracranial bleeding will continue. If the patient loses more than 75% of blood volume, direct person-to-person transfusion of fresh whole blood may be required.

Optionally, medics may cut out a portion of a helmet lining to allow a helmet to be placed on the service members head while the device is in place.

Optionally, the device is cleaned, sterilized, and recharged. The blade and membrane are replaced. The device is reused.

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described.

As used herein, the singular forms "a," "an," and "the" designate both the singular and the plural, unless expressly stated to designate the singular only.

The term "about" means that the number comprehended is not limited to the exact number set forth. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein "patient" denotes any animal in need of a burr hole in its cranium, including humans and non-human mammals.

While this specification contains many specific implementation details, these should not be construed as limitations on the scope of what may be claimed, but rather as descriptions of features specific to particular implementations. The use of any and all examples, or exemplary language (e.g., "such as") provided herein, is intended to better illuminate the embodiments and does not pose a limitation on the scope of the claims unless otherwise stated.

No language in the specification should be construed as indicating any non-claimed element as essential.

Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The construction and arrangement shown in the various example implementations are illustrative only and not restrictive in character. All changes and modifications that come within the spirit and/or scope of the described implementations are desired to be protected. It should be understood that some features may not be necessary and implementations lacking the various features may be contemplated as within the scope of the application, the scope being defined by the claims that follow.

What is claimed is:

1. An intracranial access device, comprising:
   a housing having an operator-facing side and a patient-facing side and an opening therethrough extending from the operator-facing side to the patient-facing side, configured to accommodate access to a treatment area, wherein the housing includes a surface positioned on the operator-facing side;
   at least one fastener configured to secure the device to a cranium of the patient;
   a drill mounted to the surface and structured to penetrate into the cranium; and
   a cauterizer mounted to the surface and configured to cauterize the treatment area.

2. The intracranial access device of claim 1, wherein the at least one fastener comprises adhesive.

3. The intracranial access device of claim 2, wherein the at least one fastener further comprises a plurality of bone screws.

4. The intracranial access device of claim 2, wherein the adhesive comprises open-cell foam, optionally comprising cyanoacrylate.

5. The intracranial access device of claim 1, further comprising a sealing member disposed on the patient-facing side of the housing and configured to seal the device to a patient, and optionally further comprising a storage cap configured to protect the sealing member from contaminants until use.

6. The intracranial access device of claim 5, wherein the sealing member includes closed-cell foam.

7. The intracranial access device of claim 1, wherein the cauterizer comprises an electrocautery element and a plunger, wherein the device optionally further comprises a power source configured to power the electrocautery element, and wherein operation of the cauterizer includes depressing the plunger such that the electrocautery element contacts the treatment surface.

8. The intracranial access device of claim 1, further comprising a membrane configured to seal the opening, the membrane being penetrable to provide access to the treatment area.

9. The intracranial access device of claim 1, wherein the cauterizer is axially aligned with the opening.

10. The intracranial access device of claim 1, wherein at least a portion of the housing is selectively rotatable to facilitate alternating between drilling and access to the treatment area.

11. The intracranial access device of claim 1, wherein the housing includes a user interface to facilitate locking a rotational position of the surface.

12. The intracranial access device of claim 1, further comprising:
   a retractor housed within the housing including retractor blades structured to cut into the scalp; and
   a plurality of sensors arranged on the patient-facing side of the housing and configured to identify a hemorrhage location.

13. The intracranial access device of claim 12, further comprising a sealing member disposed on the patient-facing side of the housing and configured to seal the device to a surface of a patient's head.

* * * * *